United States Patent
Furuhashi et al.

(10) Patent No.: US 7,998,419 B2
(45) Date of Patent: Aug. 16, 2011

(54) ION GENERATOR AND AIR CONDITIONER

(75) Inventors: Kenji Furuhashi, Hirakata (JP);
Naoyuki Shigemoto, Osaka (JP);
Mamoru Morikawa, Yamatokoriyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 277 days.

(21) Appl. No.: 10/556,217

(22) PCT Filed: May 10, 2004

(86) PCT No.: PCT/JP2004/006589
§ 371 (c)(1),
(2), (4) Date: Nov. 10, 2005

(87) PCT Pub. No.: WO2004/102080
PCT Pub. Date: Nov. 25, 2004

(65) Prior Publication Data
US 2006/0233660 A1 Oct. 19, 2006

(30) Foreign Application Priority Data

May 14, 2003 (JP) ................................. 2003-136358
Jul. 31, 2003 (JP) ................................. 2003-204885

(51) Int. Cl.
*A62B 7/08* (2006.01)
*A61L 2/00* (2006.01)
*A61L 2/18* (2006.01)
*A61L 9/00* (2006.01)

(52) U.S. Cl. ............... 422/123; 422/5; 422/28; 422/29; 422/120; 422/124

(58) Field of Classification Search ................. 422/28, 422/29, 5, 120, 123, 124; 250/423 R
See application file for complete search history.

(56) References Cited

U.S. PATENT DOCUMENTS

| | | | |
|---|---|---|---|
| 3,973,927 A | | 8/1976 | Furchner et al. |
| 5,259,553 A | * | 11/1993 | Shyu ............................. 236/49.3 |
| 5,428,964 A | * | 7/1995 | Lobdell ......................... 62/176.6 |
| 7,040,101 B2 | * | 5/2006 | Takeda et al. ................... 62/264 |
| 2003/0072675 A1 | * | 4/2003 | Takeda et al. .................. 422/22 |
| 2003/0086813 A1 | | 5/2003 | Fleischer |

FOREIGN PATENT DOCUMENTS

| | | |
|---|---|---|
| CN | 338946 A | 8/1998 |
| DE | 4334956 | 4/1995 |

(Continued)

OTHER PUBLICATIONS

English machine translation of JP 2000-300173.* English machine translation of JP 2003-083593.*
English machine translation of JP 2003-056878.*
J. O. Noyce et al., "Bactericidal effects of negative and positive ions generated in nitrogen on *Escherichia coli*," Journal of Electrostatics, 2002, p. 179 to 187, 54.

*Primary Examiner* — Sean E Conley
*Assistant Examiner* — Regina Yoo
(74) *Attorney, Agent, or Firm* — Birch, Stewart, Kolasch & Birch, LLP

(57) ABSTRACT

In order to efficiently kill airborne fungi in a room, an ion generator includes an ion generator, a temperature sensor for detecting a temperature, and a humidity sensor for detecting a humidity. The ion generator is controlled based on a temperature detection result detected by the temperature sensor and a humidity detection result detected by the humidity sensor. As ions are generated in accordance with the temperature and humidity, airborne fungi can efficiently be killed.

10 Claims, 17 Drawing Sheets

FOREIGN PATENT DOCUMENTS

| | | | |
|---|---|---|---|
| EP | 1293216 A1 * | 3/2003 |
| JP | 2000-300173 A | 10/2000 |
| JP | 2000300173 A * | 10/2000 |
| JP | 2003-056878 | 2/2003 |
| JP | 2003-83593 A | 3/2003 |
| JP | 2003-086329 A | 3/2003 |
| JP | 2003083593 A * | 3/2003 |
| JP | 2003-123939 A | 4/2003 |
| JP | 2003-130379 A | 5/2003 |
| WO | WO 02087034 A1 * | 10/2002 |

* cited by examiner

FIG. 4

| INDICATION OF PREDICTION PURIFICATION [TEMPERATURE AND HUMIDITY SENSOR] | INDICATION OF CLEAN SIGN [EVALUATION OF DEGREE OF IMPURENESS] | ION AUTOMATIC OPERATION | |
|---|---|---|---|
| | | CLUSTER ION INDICATOR LIGHT | ION MODE |
| × (OFF) | GREEN ⇌ ORANGE ⇌ RED | BLUE | CLEAN |
| | GREEN [0] | GREEN | ION CONTROL |
| | ORANGE [1] | BLUE | CLEAN |
| | RED [2] | | |
| ● (ON) | GREEN ⇌ ORANGE ⇌ RED | BLUE | CLEAN |
| | GREEN [0] | | |
| | ORANGE [1] | | |
| | RED [2] | | |

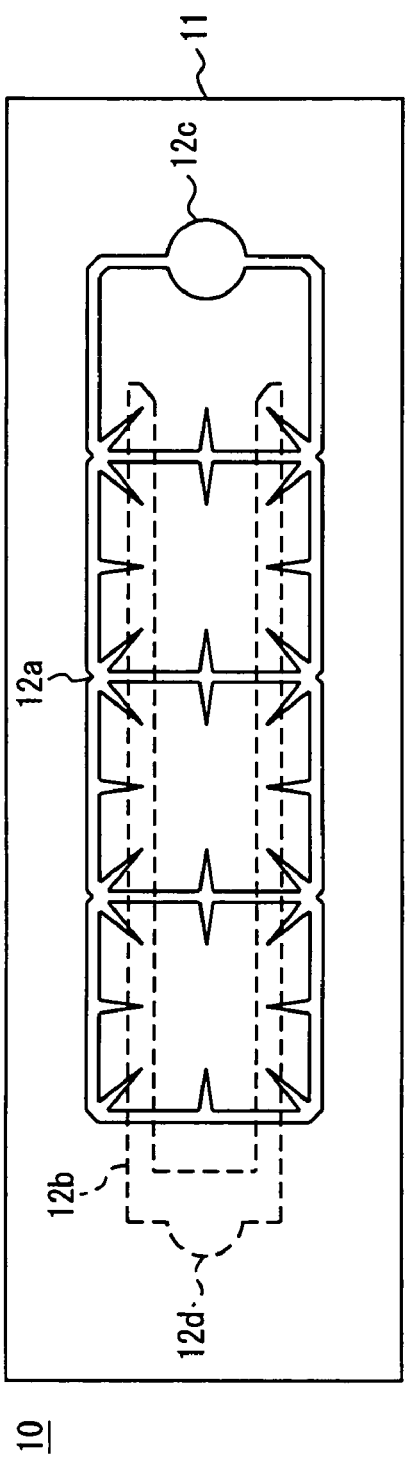
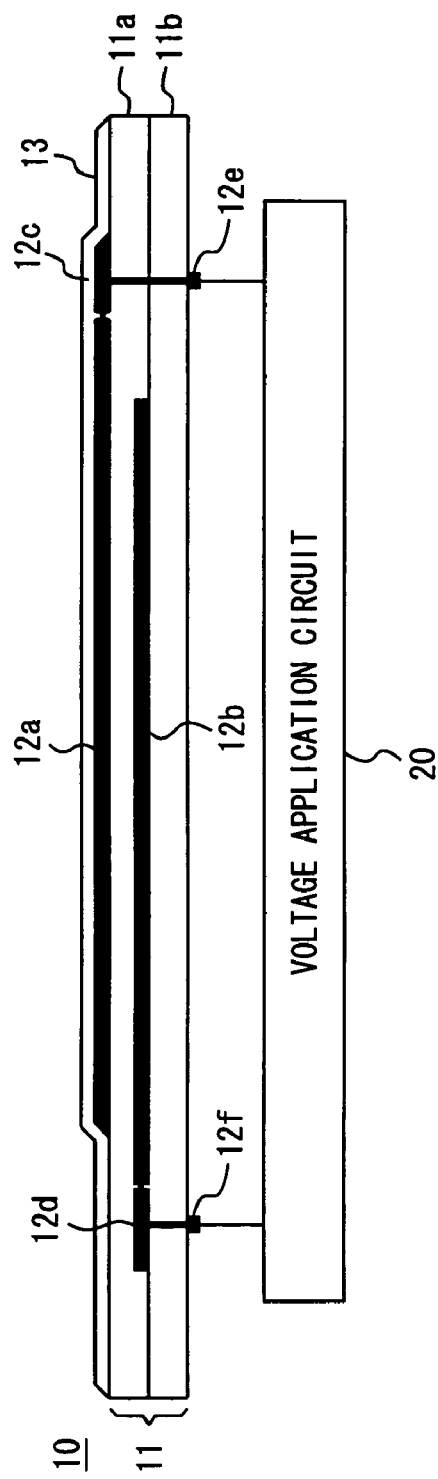

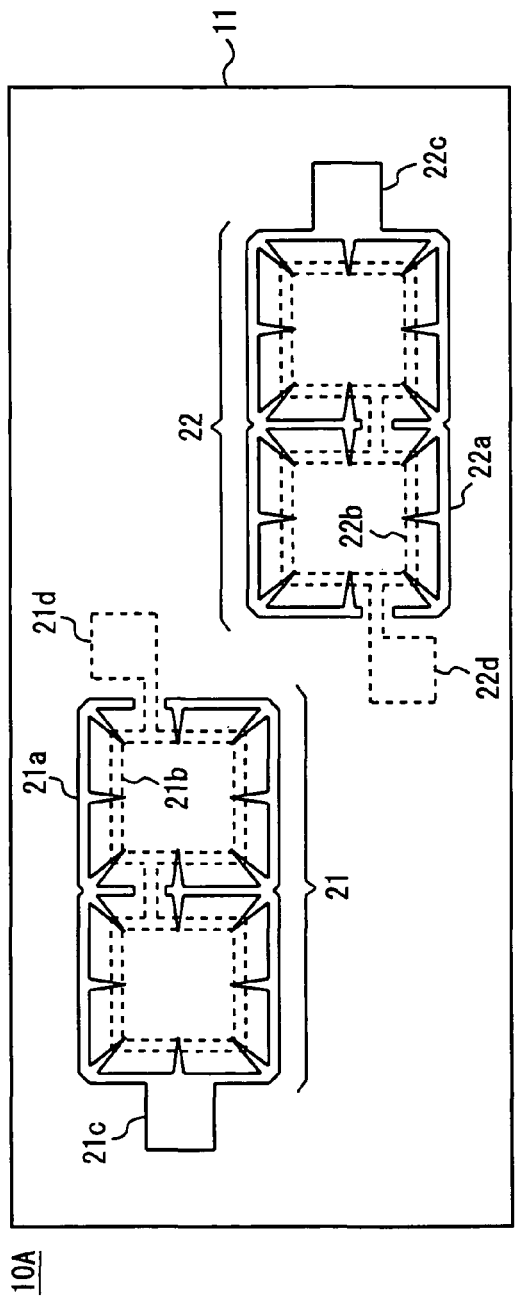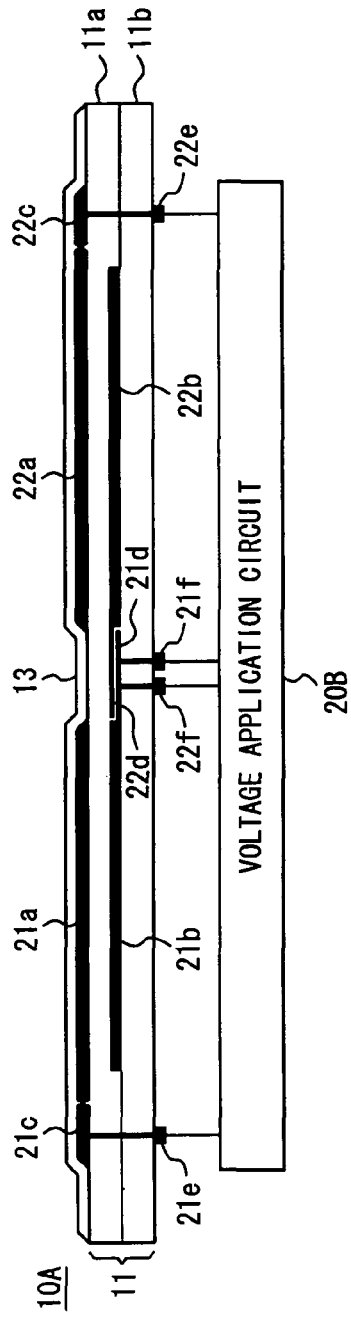

F I G. 1 4

| ODOR SENSOR OUTPUT LEVEL | DUST SENSOR OUTPUT LEVEL | RESULT OF ADDITION OF VALUES FROM BOTH SENSORS | DEGREE OF IMPURENESS | CLEAN SIGN INDICATOR LIGHT |
|---|---|---|---|---|
| UNDETECTED MODE | | | — | GREEN ⇌ ORANGE ⇌ RED |
| 0 | 0 | 0 | 0 | GREEN |
| 1 | 0 | 1 | 1 | ORANGE |
| 0 | 1 | 1 | | |
| 1 | 1 | 2 | | |
| 2 | 0 | 2 | | |
| 0 | 2 | 2 | | |
| 2 | 1 | 3 | | |
| 1 | 2 | 3 | | |
| 3 | 0 | 3 | 2 | RED |
| 0 | 3 | 3 | | |
| 3 | 1 | 4 | | |
| 1 | 3 | 4 | | |
| 2 | 2 | 4 | | |
| 3 | 2 | 5 | | |
| 2 | 3 | 5 | | |
| 3 | 3 | 6 | | |

FIG. 16

| OPERATION MODE | | FAN MOTOR OUTPUT | | VOLTAGE APPLIED TO ION GENERATOR | | | CLUSTER ION INDICATOR LIGHT |
|---|---|---|---|---|---|---|---|
| PREDICTION PURIFICATION MODE | ION MODE | FAN LEVEL NOTCH | | DUTY | TIME PERIOD OF ON | CYCLE | |
| × (OFF) | CLEAN | SILENT | FAN VOLUME 1 | 10% | 1 | 10 | ON (BLUE) |
| | | MINIMUM | FAN VOLUME 2 | 10% | 1 | 10 | |
| | | LOW | FAN VOLUME 3 | 10% | 1 | 10 | |
| | | MEDIUM | FAN VOLUME 4 | 50% | 5 | 10 | |
| | | HIGH | FAN VOLUME 5 | 50% | 5 | 10 | |
| | | MAXIMUM | FAN VOLUME 6 | 50% | 5 | 10 | |
| ● (ON) | | SILENT | FAN VOLUME 1 | 20% | 2 | 10 | SLOWLY FLASH IN CYCLE OF 5 SECONDS DURING PREDICTION PURIFICATION OPERATION (BLUE) |
| | | MINIMUM | FAN VOLUME 2 | 20% | 2 | 10 | |
| | | LOW | FAN VOLUME 3 | 20% | 2 | 10 | |
| | | MEDIUM | FAN VOLUME 4 | 100% | 10 | 10 | |
| | | HIGH | FAN VOLUME 5 | 100% | 10 | 10 | |
| | | MAXIMUM | FAN VOLUME 6 | 100% | 10 | 10 | |
| × (OFF) | ION CONTROL | SILENT | FAN VOLUME 1 | 20% | 2 | 10 | ON (GREEN) |
| | | MINIMUM | FAN VOLUME 2 | 20% | 2 | 10 | |
| | | LOW | FAN VOLUME 3 | 20% | 2 | 10 | |
| | | MEDIUM | FAN VOLUME 4 | 100% | 10 | 10 | |
| | | HIGH | FAN VOLUME 5 | 100% | 10 | 10 | |
| | | MAXIMUM | FAN VOLUME 6 | 100% | 10 | 10 | |

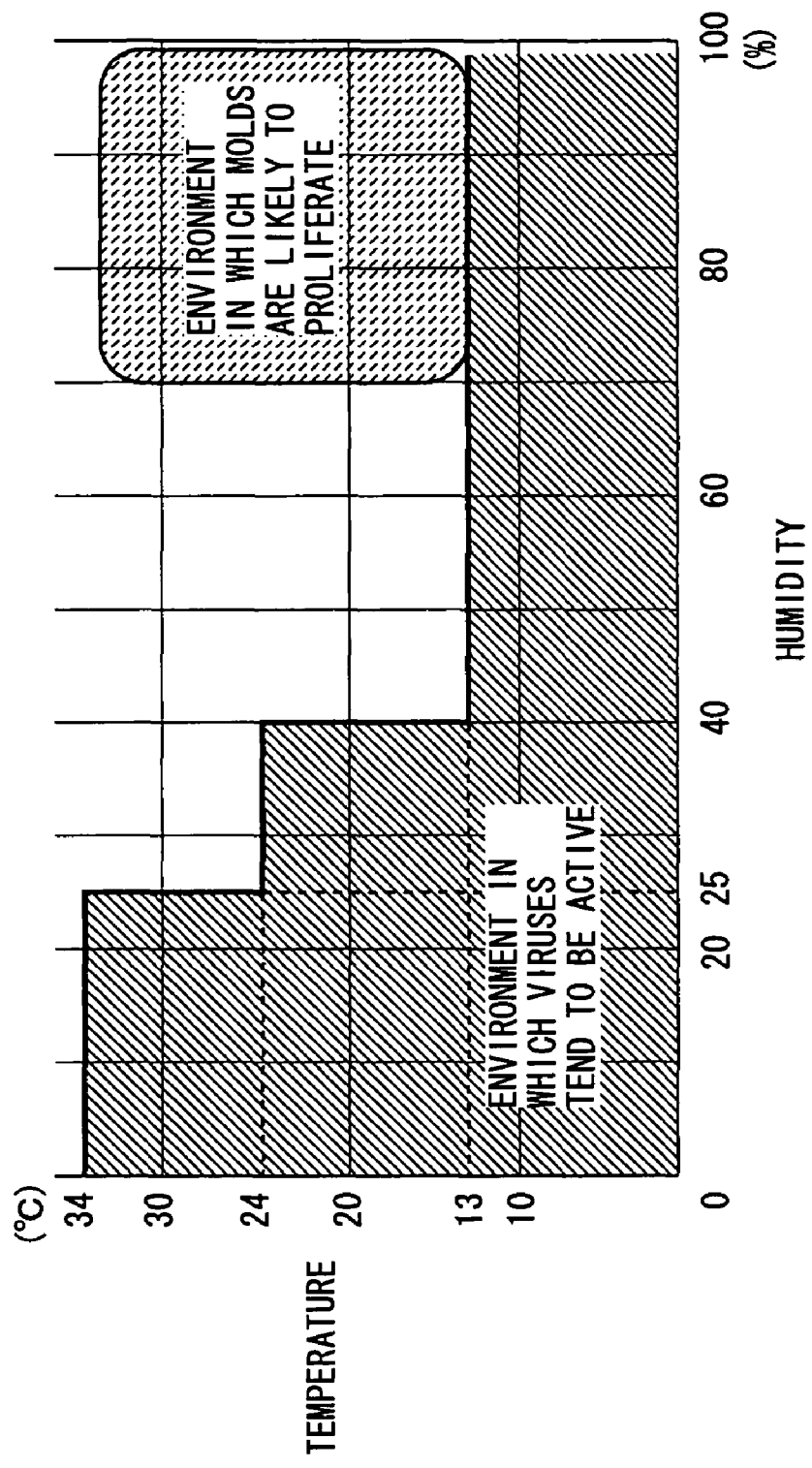

ION GENERATOR AND AIR CONDITIONER

BACKGROUND OF THE INVENTION

1. Field of the Invention

The present invention relates to an ion generator and an air conditioning apparatus, and more particularly to an ion generator and an air conditioning apparatus for sterilizing air in a room.

2. Description of the Related Art

An ion generator ionizing vapor present in a space has conventionally been known. Some of the ion generators employ creeping discharge. In the conventional ion generator, when an alternating voltage is applied to an ion generating element, positive ions and negative ions are generated. It is known that these generated positive and negative ions eliminate molds, airborne fungi or viruses in the air.

Japanese Patent Laying-Open No. 2003-83593 discloses a technique to apply such an ion generator to an air conditioner so as to suppress molds. The air conditioner disclosed in Japanese Patent Laying-Open No. 2003-83593 generates positive and negative ions from the ion generator, and determines whether or not dehumidification or cooling/heating should be performed in accordance with detected temperature or humidity in the room.

The air conditioner disclosed in Japanese Patent Laying-Open No. 2003-83593 generates positive and negative ions from the ion generator whenever it is driven. Therefore, the air conditioner generates a constant amount of positive and negative ions regardless of the temperature or humidity in the room. In other words, a prescribed amount of power is consumed in order to generate positive and negative ions.

In general, it is known that molds tend to grow in an environment of high temperature and high humidity. As to viruses, it is also known that influenza virus attains high survival ratio at low temperature and low humidity. Accordingly, concentration of the positive and negative ions in the air does not need to be high in an environment in which fungi such as molds or influenza viruses are less likely to proliferate.

Furthermore, it is known that an atmosphere containing a large amount of negative ions provides a comfortable environment for humans, with a refreshing effect. On the other hand, it is impossible to simultaneously realize a state in which a large amount of both positive and negative ions is present and a state in which a large amount of negative ions is present in a room.

SUMMARY OF THE INVENTION

The present invention was made to solve the above-described problems. An object of the present invention is to provide an ion generator capable of efficiently killing airborne fungi in a room.

Another object of the present invention is to provide an ion generator capable of preventing proliferation of molds or influenza viruses.

Yet another object of the present invention is to provide an ion generator consuming less power.

Yet another object of the present invention is to provide an ion generator capable of killing airborne fungi in the room and creating an environment comfortable for humans.

Yet another object of the present invention is to provide an air conditioning apparatus capable of efficiently killing airborne fungi.

In order to achieve the above-described objects, according to one aspect of the present invention, an ion generator includes ion generation means for generating ions, temperature and humidity detection means for detecting a temperature and a humidity in a room, and control means for controlling the ion generation means so as to generate a larger amount of ions than in a normal state when a state of the room detected by said temperature and humidity detection means attains a prescribed state. The prescribed state includes a first state at a temperature and a humidity equal to or higher than a first temperature and a first humidity respectively and a second state at a temperature and a humidity equal to or lower than a second temperature and a second humidity respectively. The second temperature is lower than the first temperature, and the second humidity is lower than the first humidity.

According to the present invention, when the state of the room attains the first state in which molds are likely to proliferate and the second state in which viruses are likely to proliferate, ions in an amount larger than that in a normal state are generated from the ion generation means. The ions are effective in killing fungi floating in the air. Therefore, the ion generator capable of preventing proliferation of molds and viruses by generating ions in an amount larger than in the normal state can be provided.

In addition, when the room is not in the prescribed state, ions in an amount comparable to that in the normal state are generated by the ion generation means. Therefore, the airborne fungi can be killed even in the normal state. Moreover, as the larger amount of ions is generated, power supplied to the ion generation means increases. As the ions are generated with low power consumption in the normal state, power consumption can be minimized. As a result, the ion generator consuming less power can be provided.

Preferably, the ion generator further includes state notification means for notification of temperature detection result and/or humidity detection result, and instruction accepting means for accepting an instruction to start control of the ion generation means. Control of the ion generation means is started in response to acceptance of the instruction by the instruction accepting means.

According to the present invention, control of the ion generation means is started in response to acceptance of the instruction by the instruction accepting means. Therefore, the ion generation means can be controlled when a user desires.

Preferably, the ion generation means generates positive ions and negative ions.

Preferably, the first state refers to a state in which the temperature detected by the temperature and humidity detection means is at least 25° C. and the humidity detected by the temperature and humidity detection means is at least 70%, and the second state refers to a state in which the temperature detected by the temperature detection means is at most 18° C. and the humidity detected by the humidity detection means is at most 40%.

In the first state, molds are likely to proliferate, and in the second state, viruses are likely to proliferate. Ions are effective in killing fungi floating in the air. Therefore, an ion generator capable of preventing proliferation of molds and viruses in a state where molds and viruses are likely to proliferate can be provided.

Preferably, the ion generator further includes impureness detection means for detecting impureness in the room. The control means causes the ion generation means to generate negative ions more than positive ions, when a state of the room detected by the temperature and humidity detection means does not attain the prescribed state and when a prescribed degree of impureness is not detected by the impureness detection means.

According to the present invention, when the state of the room does not attain the prescribed state and when the prescribed degree of impureness is not detected, more negative ions than positive ion are generated. When negative ions are contained in the air in an amount larger than that of positive ions, refreshing effect for humans can be obtained. Therefore, the ion generator capable of creating an environment comfortable for humans, for example, when the room is clean and not in an environment in which airborne fungi are like to proliferate can be provided.

Preferably, the impureness detection means includes a dust sensor.

Preferably, the impureness detection means includes an odor sensor.

According to another aspect of the present invention, an ion generator includes: ion generation means for generating ions; impureness detection means for detecting impureness in a room; temperature and humidity detection means for detecting a temperature and a humidity in the room; and control means for controlling an amount of ions generated by the ion generation means when a state of the room detected by the impureness detection means and the temperature and humidity detection means attains a prescribed state. The prescribed state includes a first state at a temperature and a humidity equal to or higher than a first temperature and a first humidity respectively, and a second state at a temperature and a humidity equal to or lower than a second temperature and a second humidity respectively. The second temperature is lower than the first temperature, and the second humidity is lower than the first humidity.

According to the present invention, an amount of ions generated from the ion generation means can be made different depending on whether the state of the room detected by the impureness detection means and the temperature and humidity detection means attains the first state in which molds are likely to proliferate and the second state in which viruses are likely to proliferate. Therefore, an ion generator capable of preventing proliferation of molds and viruses can be provided. When the air is impure, it is probable that airborne fungi are contained. If an amount of ion generation is increased when the air in the room is impure and the room is in an environment where airborne fungi are likely to proliferate, proliferation of the airborne fungi can efficiently be prevented.

Preferably, the control means cause the ion generation means to generate more negative ions than positive ions, when a degree of impureness detected by the impureness detection means does not attain a prescribe value and when a state of the room detected by the temperature and humidity detection means does not attain the prescribed state.

According to the present invention, when the degree of impureness does not attain the prescribed value and when the state of the room does not attain the prescribed state, negative ions are generated in an amount larger than that of positive ions. When negative ions are contained in the air in an amount larger than that of positive ions, refreshing effect can be obtained. Therefore, when there is smaller amount of airborne fungi in the room and an environment is such that fungi are unlikely to proliferate, an environment comfortable for humans can be created.

Preferably, the impureness detection means includes a dust sensor.

Preferably, the impureness detection means includes an odor sensor.

According to another aspect of the present invention, an air conditioning apparatus includes cleaning means for lowering a degree of impureness in a room, and the ion generator described above.

According to the present invention, as impureness in the room is lowered, an environment in which airborne fungi are less likely to proliferate can be created. Therefore, an air conditioning apparatus capable of efficiently killing the airborne fungi can be provided.

According to yet another aspect of the present invention, an air conditioning apparatus includes dehumidifying and humidifying means for adjusting a humidity in a room, and the ion generator described above.

According to the present invention, as the humidity in the room is adjusted, an environment in which airborne fungi are less likely to proliferate can be created. Therefore, an air conditioning apparatus capable of efficiently killing the airborne fungi can be provided.

According to yet another aspect of the present invention, an air conditioning apparatus includes cooling and heating means for adjusting a temperature in a room, and the ion generator described above.

According to the present invention, as the temperature in the room is adjusted, an environment in which airborne fungi are less likely to proliferate can be created. Therefore, an air conditioning apparatus capable of efficiently killing the airborne fungi can be provided.

According to yet another aspect of the present invention, an air conditioning apparatus includes dust detection means for detecting dust in a room, odor detection means for detecting odor in the room, temperature detection means for detecting a temperature, and humidity detection means for detecting a humidity. The air conditioning apparatus controls purifying of air based on the dust detection means, the odor detection means, the temperature detection means, and the humidity detection means.

According to another aspect of the present invention, an air conditioning apparatus includes dust detection means for detecting dust in a room, odor detection means for detecting odor in the room, temperature detection means for detecting a temperature, and humidity detection means for detecting a humidity. The air conditioning apparatus purifies air in the room in accordance with a value detected by the detection means.

According to yet another aspect of the present invention, an air conditioning apparatus includes dust detection means for detecting dust in a room, odor detection means for detecting odor in the room, and temperature and humidity detection means for detecting a temperature and a humidity in the room. The air conditioning apparatus switches an operation mode of means for purifying air in the room from low to high such that performance thereof is improved when a state of the room detected by the dust detection means, the odor detection means and the temperature and humidity detection means attains a prescribed state.

Preferably, the prescribed state includes a first state at a temperature and a humidity equal to or higher than a first temperature and a first humidity respectively, and a second state at a temperature and a humidity equal to or lower than a second temperature and a second humidity respectively.

Preferably, when a value detected by the dust detection means and the odor detection means does not attain a prescribed value and when a state of the room detected by the temperature and humidity detection means does not attain the prescribed state, the operation mode of the means for purifying the air in the room is not switched.

According to the present invention, as impureness in the room is lowered, an environment in which airborne fungi are less likely to proliferate can be created. Therefore, an air conditioning apparatus capable of efficiently killing the airborne fungi can be provided.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 4 shows a relation between an operation mode of the air conditioning apparatus and display contents on the display portion in the first embodiment.

FIG. 7A is a plan view schematically showing a configuration of an ion generator in the first embodiment.

FIG. 7B is a side view schematically showing the configuration of the ion generator in the first embodiment.

FIG. 12A shows a variation of the ion generator in the first embodiment.

FIG. 12B shows another variation of the ion generator in the first embodiment.

FIG. 14 shows an example of a degree of impureness evaluation table used in the air conditioning apparatus in the first embodiment.

FIG. 16 shows a relation between an operation mode for air-conditioning and a fan motor output and a voltage applied to the ion generator in the first embodiment.

FIG. 17 shows one example of a prescribed state.

DETAILED DESCRIPTION OF THE INVENTION

Figure 1A:
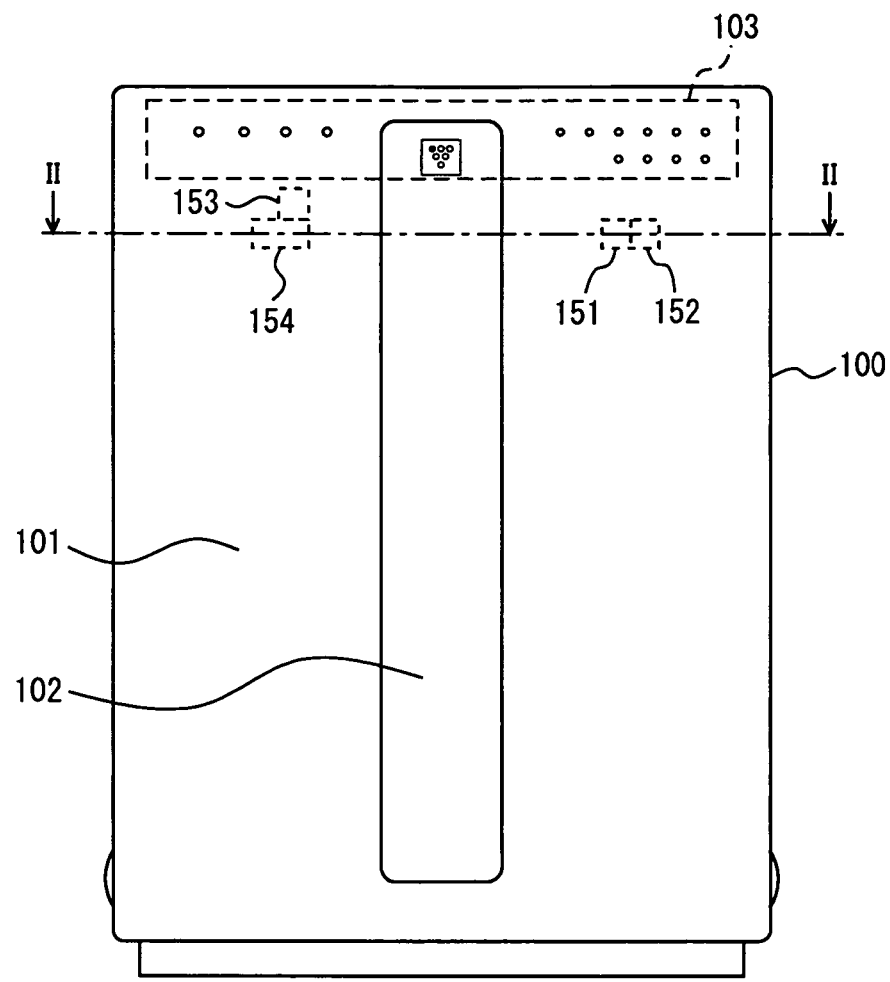
FIG. 1A is a front view of an air conditioning apparatus in a first embodiment of the present invention.

In the following, embodiments of the present invention will be described with reference to the figures. It is noted that the same reference characters refer to the same or corresponding components and denotation and functions thereof are also the same. Therefore, detailed description thereof will not be repeated.

First Embodiment

Figure 1B:
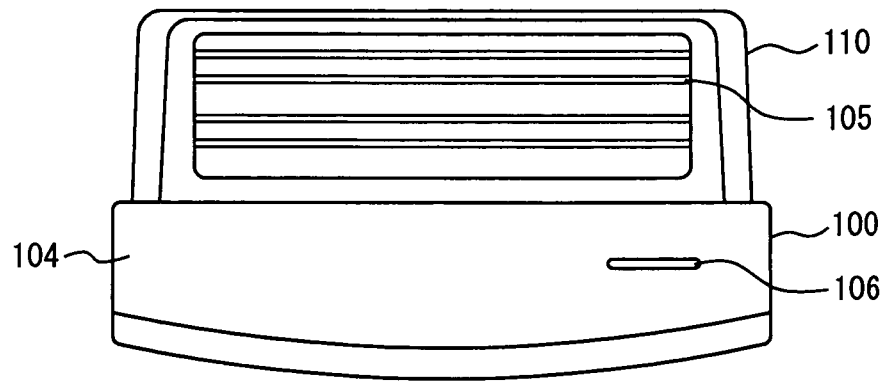
FIG. 1B is a plan view of the air conditioning apparatus in the first embodiment of the present invention.

Initially, an air conditioning apparatus in the first embodiment will be described. FIGS. 1A and 1B show appearance of an air conditioning apparatus in one embodiment of the present invention. FIG. 1A shows a front view, while FIG. 1B shows a plan view. Referring to FIGS. 1A and 1B, an air conditioning apparatus 100 includes a front panel 101 on a front face of a main unit 110. Front panel 101 is attached with a prescribed space in front of main unit 110 for air intake. Front panel 101 has an opening for taking air into main unit 110 in the center.

In the rear of the opening of front panel 101, a central panel 102 is attached to main unit 110. As front panel 101 and central panel 102 block the view, an inner portion of the main unit cannot be seen from the front. A display portion 103 is provided in an upper portion of front panel 101. Display portion 103 also includes an upper portion of central panel 102.

A top panel 104 is provided on the top of main unit 110. Top panel 104 includes a power switch 106. In addition, top panel 104 includes an outlet 105 for emitting purified air.

Air conditioning apparatus 100 includes a temperature sensor 151, a humidity sensor 152, a dust sensor 153, and an odor sensor 154 in main unit 110 behind front panel 101.

Figure 2:
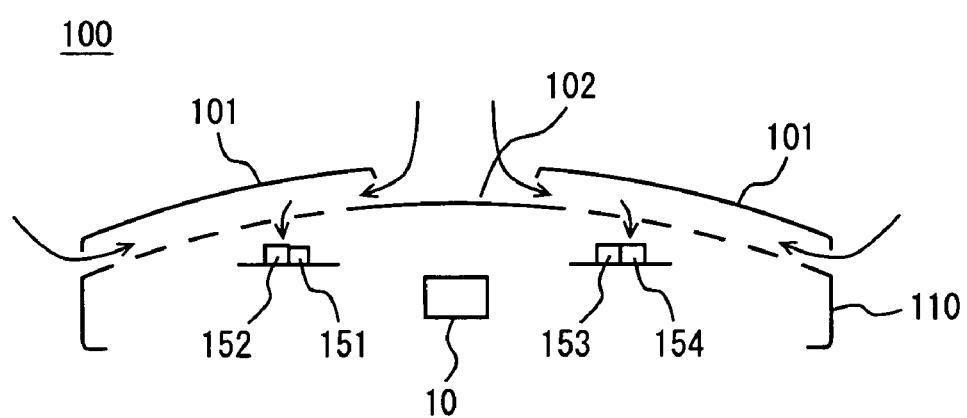
FIG. 2 is a cross-sectional view along the line II-II in FIG. 1A.

FIG. 2 is a cross-sectional view along the line II-II in FIG. 1A. It is noted that arrows in the drawing indicate flow of the air. Referring to FIG. 2, air conditioning apparatus 100 includes temperature sensor 151, humidity sensor 152, dust sensor 153, and odor sensor 154 in main unit 110. Front panel 101 is attached to main unit 110 with a gap for air intake. This gap serves as an air inlet. In addition, central panel 102 is attached to main unit 110 in the rear of the opening in the center of front panel 101. This opening also serves as an air inlet for taking the air in the room into the main unit 110.

An ion generator 10 is provided in main unit 110 under top panel 104. Though not shown, an air purifying filter for purifying the air and a fan motor and a fan for flowing the air are further provided between the air inlet and outlet 105.

Air conditioning apparatus 100 drives the contained fan motor so as to rotate the fan and so as to generate air flow. The air flow is directed from the air inlet toward outlet 105. In this manner, the air is introduced from the air inlet into main unit 110, and carried to temperature sensor 151, humidity sensor 152, dust sensor 153, and odor sensor 154. Further, the air passes through a deodorizing filter to reach outlet 105, from which the air is discharged to the room. As ion generator 10 is provided between the deodorizing filter and outlet 105, the air is ionized when the air flows in the vicinity of ion generator 10. Therefore, the air exiting from outlet 105 contains ions.

In air conditioning apparatus 100 in the present embodiment, temperature sensor 151, humidity sensor 152, dust sensor 153, and odor sensor 154 are provided in the vicinity of the air inlet. Therefore, room temperature and humidity as well as an amount of dust and odor can accurately be detected.

It is noted that attachment positions of temperature sensor 151, humidity sensor 152, dust sensor 153, and odor sensor 154 are not limited to the above-mentioned example. Such positions are not limited, so long as those sensors are located around the air inlet in air conditioning apparatus 100.

Figure 3:
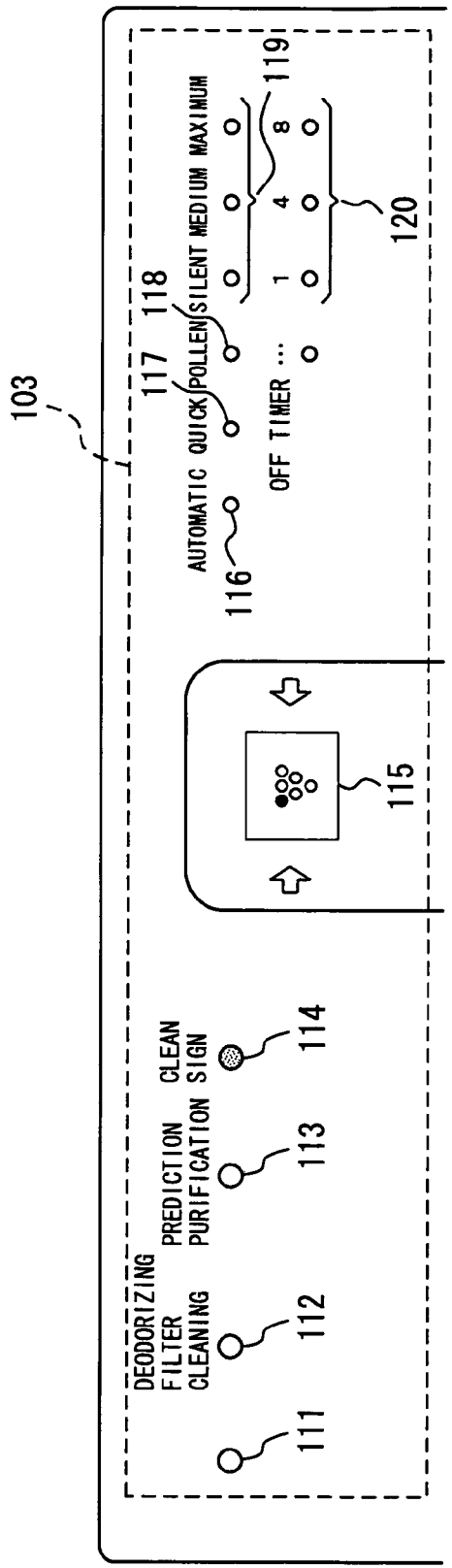
FIG. 3 illustrates a display portion of the air conditioning apparatus in the first embodiment.

FIG. 3 illustrates the display portion of the air conditioning apparatus in the first embodiment. Referring to FIG. 3, display portion 103 includes a light receiving portion 111 for receiving an infrared ray from a remote controller for remote control of air conditioning apparatus 100; a deodorizing filter cleaning indicator light 112 for notifying a user of a time to clean the deodorizing filter provided in air conditioning apparatus 100; a prediction purification indicator light 113 indicating whether or not an operation mode of air conditioning apparatus 100 is set to a prediction purification mode; a clean sign indicator light 114 indicating a degree of impureness of the air in the room; a cluster ion indicator light 115 indicating a drive mode of ion generator 10; an automatic operation indicator light 116, a quick mode indicator light 117 and a pollen mode indicator light 118 for indicating an operation mode of air conditioning apparatus 100; three manual state indicator lights 119 indicating a drive state of the fan motor when the operation mode is set to a manual mode; and an off timer indicator light 120 indicating an off-timer setting time.

Deodorizing filter cleaning indicator light 112 illuminates when a value for accumulated operation time of air conditioning apparatus 100 exceeds a predetermined deodorizing filter cleaning time, and otherwise it turns off. In this manner, the user can be notified of a timing to clean the deodorizing filter in air conditioning apparatus 100.

Operation modes of air conditioning apparatus 100 include an automatic mode, a quick mode, a pollen mode, and a manual mode. The automatic operation mode refers to an operation mode in which the fan level of the fan motor and an amount of ion generation by ion generator 10 are automatically controlled in accordance with a degree of impureness determined by outputs from dust sensor 153 and odor sensor 154. When air conditioning apparatus 100 operates in the automatic operation mode, automatic operation indicator light 116 illuminates. The quick mode refers to an operation mode in which the fan motor and ion generator 10 operate at maximum power. When air conditioning apparatus 100 operates in the quick mode, quick mode indicator light 117 illuminates. The pollen mode refers to an operation mode in which the fan motor and the ion generator are driven so as to attain output suitable for eliminating pollens. The outputs of the fan motor and ion generator 10 suitable for eliminating pollens are predetermined and stored. When air conditioning apparatus 100 operates in the pollen mode, pollen mode indicator light 118 illuminates. The manual mode refers to an operation mode in which the fan motor and ion generator 10 are driven so as to attain output designated by the user. When air conditioning apparatus 100 operates in the manual mode, any one of three manual state indicators 119 indicating a drive state of the fan motor of silent, medium and maximum illuminates in accordance with the output designated by the user. As to ion generator 10, cluster ion indicator light 115 illuminates in a color described later, in accordance with the output designated by the user.

Off timer indicator light 120 indicates a timer setting time designated by the user. Any one of three off timer indicator lights 120 illuminates.

Clean sign indicator light 114 indicates a degree of impureness of the air in the room. In the present embodiment, three levels of the degree of impureness are set. The degree of impureness is determined by outputs from dust sensor 153 and odor sensor 154. Clean sign indicator light 114 illuminates in green, orange or red, in accordance with the degree of impureness. Clean sign indicator light 114 illuminates in green, corresponding to "0" degree of impureness indicating the lowest impureness level; it illuminates in orange, corresponding to "1" degree of impureness indicating an intermediate level of impureness; and it illuminates in red, corresponding to "2" degree of impureness indicating the highest impureness level.

Cluster ion indicator light 115 indicates a drive mode of ion generator 10. Drive modes of ion generator 10 include an ion control mode and a clean mode. The ion control mode refers to a mode in which negative ions in an amount larger than that of positive ions are generated from ion generator 10, or to a mode in which solely negative ions are generated. The clean mode refers to a mode in which positive ions and negative ions are generated in substantially the same amount from ion generator 10, respectively. Cluster ion indicator light 115 illuminates in green when ion generator 10 operates in the ion control mode, while it illuminates in blue when ion generator 10 operates in the clean mode. When ion generator 10 is not driven, cluster ion indicator light 115 turns off.

The operation mode of air conditioning apparatus 100 further includes a prediction purification mode. The prediction purification mode refers to an operation mode when the temperature and the humidity in the room attain a prescribed state. Here, the prescribed state refers to a first state in which the temperature is at least 25° C. and the humidity is at least 70%, or a second state in which the temperature is at most 18° C. and the humidity is at most 40%. Prediction purification indicator light 113 indicates whether or not air conditioning apparatus 100 operates in the prediction purification mode, that is, whether or not the air in the room is in the prescribed state. Prediction purification indicator light 113 illuminates when air conditioning apparatus 100 operates in the prediction purification mode, and otherwise it turns off.

When air conditioning apparatus 100 operates in the prediction purification mode, ion generator 10 is driven in the clean mode. Here, an amount of generation of positive and negative ions is increased, as compared with when air conditioning apparatus 100 is not in the prediction purification mode. When air conditioning apparatus 100 is not in the prediction purification mode, it is in a normal state. In other words, in the prediction purification mode, ion generator 10 is driven and controlled so as to generate ions in an amount larger than that in the normal state. This will be described in detail later.

FIG. 4 shows a relation between the operation mode of air conditioning apparatus 100 and display contents on display portion 103 in the first embodiment. Referring to FIG. 4, when the prediction purification indicator light turns off, clean sign indicator light 114 illuminates in either green, orange or red, in accordance with the degree of impureness. Here, it takes a prescribed time from turn-on of power switch 106 of air conditioning apparatus 100 until outputs from dust sensor 153 and odor sensor 154 are stabilized. The degree of impureness is not determined during a period from turn-on of the power until the outputs from dust sensor 153 and odor sensor 154 are stabilized. Therefore, during such a time period, clean sign indicator light 114 sequentially illuminates in an order of green, orange and red each for one second. Therefore, if the user observes the sequential illumination of clean sign indicator light 114 in different colors, the user can know that the degree of impureness is not yet detected.

When the degree of impureness is determined as "0", ion generator 10 is driven in the ion control mode. Accordingly, cluster ion indicator light 115 illuminates in green. In addition, when the degree of impureness is determined as either "1" or "2", ion generator 10 is driven in the clean mode. Here, cluster ion indicator light 115 illuminates in blue. During a prescribed time period until the degree of impureness is found, the ion generator is driven in the clean mode, during which cluster ion indicator light 115 illuminates in blue.

When prediction purification indicator light 113 illuminates, clean sign indicator light 114 illuminates in accordance with the degree of impureness, in a manner similar to that when prediction purification indicator light 113 turns off. On the other hand, in the prediction purification mode, ion generator 10 is driven in the clean mode. In the clean mode, the ion generator is driven such that positive and negative ions in an amount larger than when not in the prediction purification mode are generated. Even in such a case, cluster ion indicator light 115 illuminates in blue. Therefore, if cluster ion indicator light 115 illuminates in blue and prediction purification indicator light 113 illuminates, the operation mode of ion generator 10 is in the clean mode. In the clean mode, ion generator 10 generates positive and negative ions in an amount larger than when not in the prediction purification mode.

Figure 5:
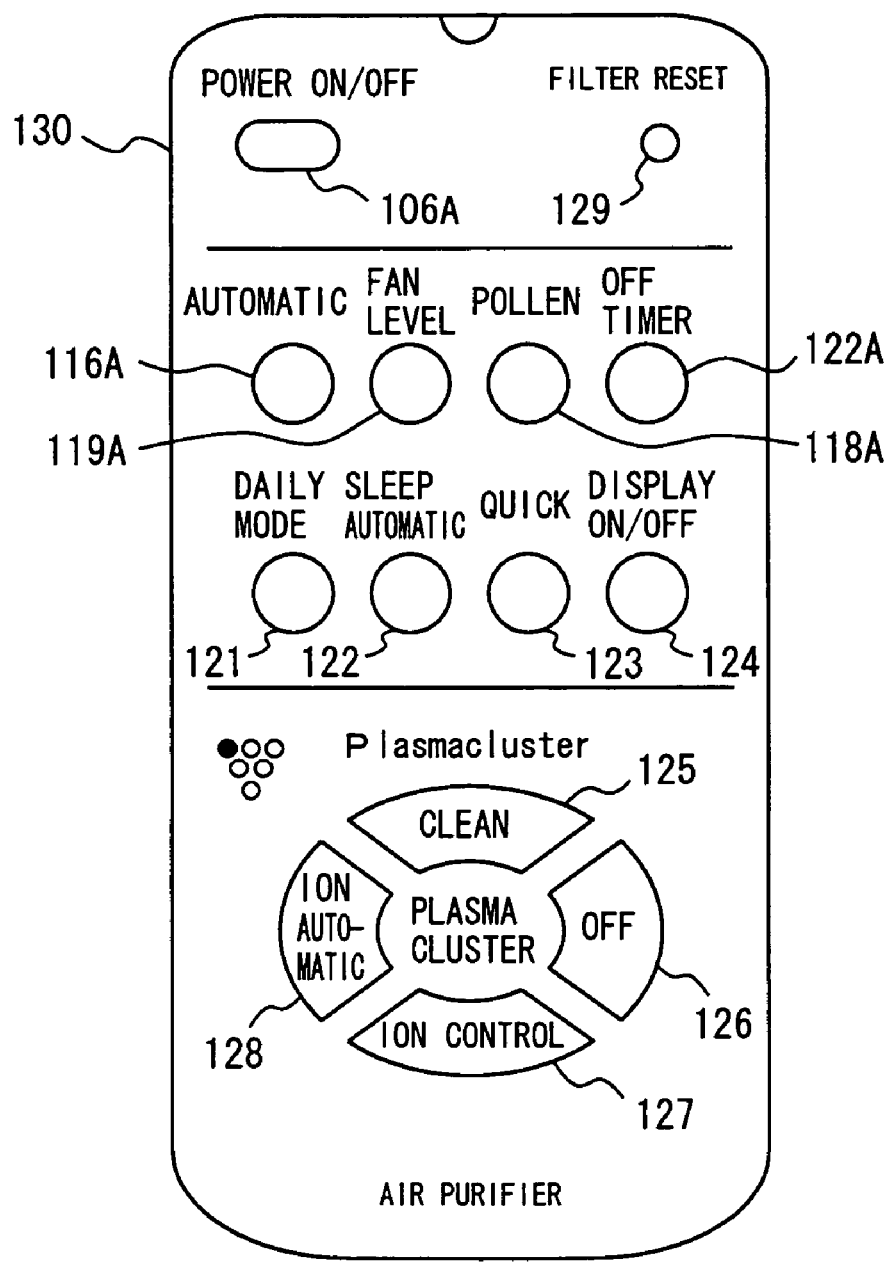
FIG. 5 is a plan view of a remote controller of the air conditioning apparatus in the first embodiment.

FIG. 5 is a plan view of remote controller 130 of air conditioning apparatus 100 in the first embodiment. Remote controller 130 includes a power switch 106A for switching on/off of the power of air conditioning apparatus 100; a filter reset button 129 for resetting accumulated operation time after cleaning the deodorizing filter; an automatic button 116A for setting the operation mode of air conditioning apparatus 100 to the automatic mode; a fan level button 119A for switching to the manual mode and designating a fan level of the fan motor; a pollen button 118A for setting the pollen mode; an off-timer button 122A for setting an off-timer setting time; a daily mode button 121 for setting a daily mode; a sleep automatic button 122 for setting a sleep automatic mode; a quick button 123 for setting the quick mode; a display switch button 124 for switching on/off of display on display portion 103; and setting buttons 125 to 128 for manually setting the drive mode of ion generator 10.

Remote controller 130 outputs a signal of infrared light in accordance with the pressed switch. When light receiving portion 111 in air conditioning apparatus 100 receives the signal of infrared light, air conditioning apparatus 100 is driven in response to the signal of infrared light.

Though remote controller 130 using the infrared light is exemplarily described in the first embodiment, a communication medium between remote controller 130 and air conditioning apparatus 100 is not limited to the infrared light. For example, an electromagnetic wave or an acoustic wave can be employed. That is, any means allowing radio communication may be used, without limited to the infrared light.

When automatic button 116A is pressed, air conditioning apparatus 100 sets the operation mode to the automatic mode and operates. When fan level button 119A is pressed, air conditioning apparatus 100 changes the number of revolution of the fan motor, i.e., the fan level, in the order of silent, medium and maximum, every time fan level button 119A is pressed. When pollen button 118A is pressed, air conditioning apparatus 100 sets the operation mode to the pollen mode and operates. Every time the off-timer button 122A is pressed, the off-timer setting time is sequentially set in the order of 1 hour, 4 hours and 8 hours.

When daily mode button 121 is pressed, air conditioning apparatus 100 sets the operation mode to the daily mode and operates. When sleep automatic mode button 122 is pressed, air conditioning apparatus 100 sets the number of revolution of the fan motor to the number adapted to the silent mode.

When quick button 123 is pressed, air conditioning apparatus 100 sets the operation mode to the quick mode and operates.

When any of setting buttons 125 to 128 is pressed, the drive mode of ion generator 10 is switched. When setting button 126 is pressed, application of a voltage to ion generator 10 is stopped so as to stop drive of ion generator 10. In air conditioning apparatus 100, cluster ion indicator light 115 turns off. When setting button 125 is pressed, ion generator 10 is driven in the clean mode. In air conditioning apparatus 100, cluster ion indicator light 115 illuminates in blue.

When setting button 127 is pressed, ion generator 10 is driven in the ion control mode in air conditioning apparatus 100, and cluster ion indicator light 115 illuminates in green.

When setting button 128 is pressed, air conditioning apparatus 100 drives ion generator 10 in the automatic mode. Here, the automatic mode is determined based on outputs from temperature sensor 151, humidity sensor 152, dust sensor 153, and odor sensor 154. Control over the drive state of ion generator 10 in the automatic mode will be described in detail later.

Figure 6:
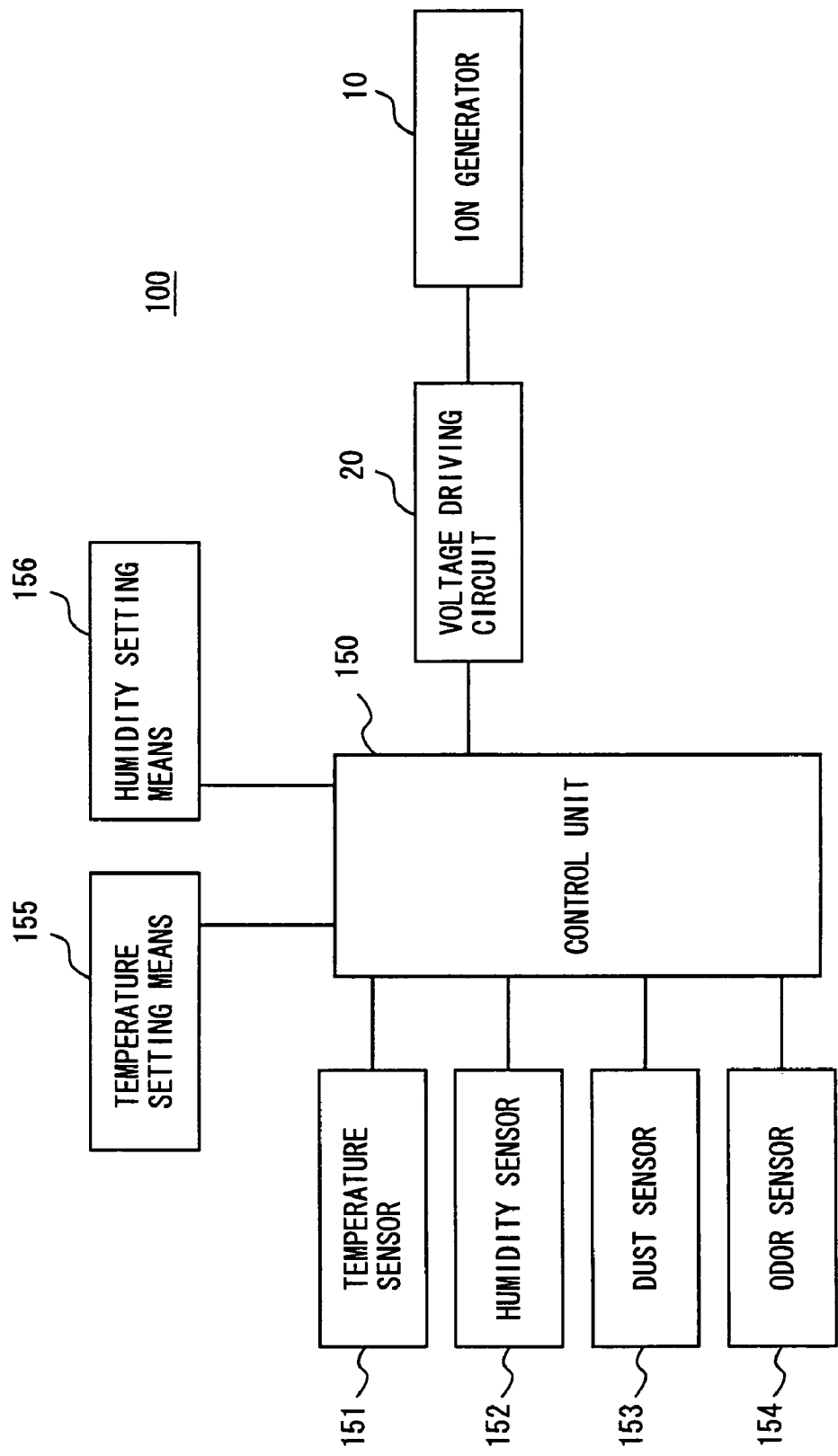
FIG. 6 is a circuit block diagram of the air conditioning apparatus in the first embodiment.

FIG. 6 is a circuit block diagram of air conditioning apparatus 100 in the first embodiment. Referring to FIG. 6, ion generator 10 includes a control unit 150 for overall control of ion generator 10; temperature sensor 151 for detecting a temperature, humidity sensor 152 for detecting a humidity, dust sensor 153 for detecting dust, and odor sensor 154 for detecting odor, each of which is connected to control unit 150; temperature setting means 155 for setting a temperature; humidity setting means 156 for setting a humidity; and a voltage driving circuit 20 for applying a voltage to ion generator 10. Ion generator 10 is connected to voltage driving circuit 20.

As described above, air conditioning apparatus 100 includes the prediction purification mode as the operation mode. The prediction purification mode refers to the operation mode set when the temperature and the humidity in the room attain the prescribed state. Temperature setting means 155 and humidity setting means 156 are means for setting threshold values for determining the prescribed state. Temperature setting means 155 and humidity setting means 156 are implemented by a button switch or a slide switch provided in main unit 110 and serve to set the temperature and the humidity. Temperature setting means 155 and humidity setting means 156 may be provided in remote controller 130 so that the set temperature and humidity are transmitted from remote controller 130 to air conditioning apparatus 100.

FIGS. 7A and 7B schematically show a configuration of the ion generator in the first embodiment. FIG. 7A is a plan view schematically showing the configuration of ion generator 10, while FIG. 7B is a side view of ion generator 10. Ion generator 10 includes a dielectric 11, a discharge electrode 12a, an induction electrode 12b, and a coating layer 13. When a voltage is applied to discharge electrode 12a and induction electrode 12b, discharge occurs between discharge electrode 12a and induction electrode 12b, whereby both positive and negative ions or negative ions are generated.

Dielectric 11 is implemented as a plate-like component formed by laminating an upper dielectric 11a and a lower dielectric 11b. Discharge electrode 12a is formed integrally with upper dielectric 11a on the surface of upper dielectric 11a. Induction electrode 12b is formed between upper dielectric 11a and lower dielectric 11b, and arranged facing to discharge electrode 12a. Desirably, insulation resistance between discharge electrode 12a and induction electrode 12b is uniform, and discharge electrode 12a is parallel to induction electrode 12b.

In ion generator 10, discharge electrode 12a and induction electrode 12b are arranged opposing to each other, on a surface and a back surface of upper dielectric 11a respectively. Accordingly, a distance between discharge electrode 12a and induction electrode 12b can be constant. In this manner, a discharge state between discharge electrode 12a and induction electrode 12b is stabilized, and both positive and negative ions or negative ions can suitably be generated.

A discharge electrode contact 12e is electrically connected to discharge electrode 12a via a connection terminal 12c provided on the surface where discharge electrode 12a is located. One end of a conductive lead is connected to discharge electrode contact 12e while the other end thereof is connected to voltage application circuit 20, so that discharge electrode 12a and voltage application circuit 20 can electrically be connected. An induction electrode contact 12f is electrically connected to induction electrode 12b via a connection terminal 12d provided on the surface where induction electrode 12b is located. One end of a lead implemented by a copper wire is connected to induction electrode contact 12f while the other end thereof is connected to voltage application circuit 20, so that induction electrode 12b and voltage application circuit 20 can electrically be connected.

Figure 8:
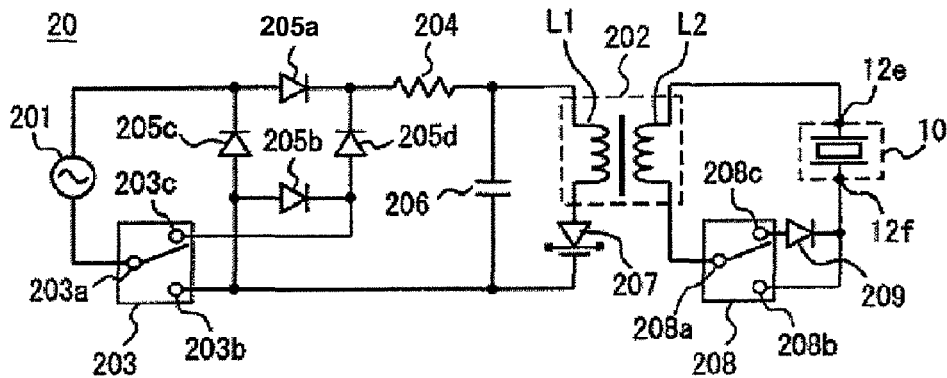
FIG. 8 is a circuit diagram of a voltage application circuit in the first embodiment.

FIG. 8 is a circuit diagram of voltage application circuit 20 in the first embodiment. Referring to FIG. 8, voltage application circuit 20 includes an AC power supply 201, a switching transformer 202, a switch relay 203, a resistor 204, diodes 205a to 205d, a capacitor 206, and an SIDAC (R) 207. SIDAC (R) 207 is one type of silicon control rectifier SCR and manufactured by Shindengen Electric Manufacturing Co., Ltd.

One end of AC power supply 201 is connected to the anode of diode 205a and the cathode of diode 205c, while the other end thereof is connected to a common terminal 203a of switch relay 203. The cathode of diode 205a is connected to one end of resistor 204 and the cathode of diode 205d. The other end of resistor 204 is connected to one end of a primary coil L1 of transformer 202 and one end of capacitor 206. The other end of primary coil L1 is connected to the anode of SIDAC (R) 207. The other end of capacitor 206 is connected to the cathode of SIDAC (R) 207, of which connection node is connected to one selection terminal 203b in switch relay 203 and respective anodes of diodes 205b and 205c. The cathode of diode 205b is connected to the anode of diode 205d, of which connection node is connected to the other selection terminal 203c of switch relay 203. One end of a secondary coil L2 of transformer 202 is connected to discharge electrode contact 12e of ion generator 10, while the other end thereof is connected to a common terminal 208a of a relay 208. One selection terminal 208c in relay 208 is connected to the anode of a diode 209, and the cathode of diode 209 is connected to induction electrode contact 12f Induction electrode contact 12f of ion generator 10 is connected to the other selection terminal 208b in relay 208 and the anode of diode 209.

In voltage application circuit 20 configured as described above, when air conditioning apparatus 100 is not in the prediction purification mode and when the drive mode of ion generator 10 is set to the clean mode, selection terminal 203b is selected in switch relay 203 and selection terminal 208b is selected in switch relay 208.

Here, an output voltage of AC power supply 201 is subjected to half-wave rectification in diode 205a, then lowered by resistor 204, and applied to capacitor 206. When capacitor 206 is charged and a voltage across the capacitor attains a prescribed threshold value, SIDAC (R) 207 attains an on state and the charged voltage of capacitor 206 is discharged.

Accordingly, a current flows through primary coil L1 in transformer 202 to transmit energy to secondary coil L2, whereby a pulse voltage is applied to ion generator 10. Immediately thereafter, SIDAC (R) 207 attains an off state and charge of capacitor 206 is started again.

By repeating charge and discharge described above, an AC impulse voltage in FIG. 9A (pp (Peak-to-Peak) value: 3.5 [kV], the number of times of discharge: 120 [times per second], for example) is applied between discharge electrode 12a and induction electrode 12b of ion generator 10. Here, corona discharge occurs in the vicinity of ion generator 10, and the ambient air is ionized. That is, $H^+(H_2O)_m$ which is a positive ion is generated when a positive voltage is applied, while $O_2^-(H_2O)_n$ which is a negative ion is generated when a negative voltage is applied (m, n are 0 or any natural number). More specifically, the AC voltage is applied between discharge electrode 12a and induction electrode 12b of ion generator 10. Then, oxygen or moisture in the air is energized by electrolytic dissociation and ionized, whereby ions mainly containing $H^+(H_2O)_m$ (m is 0 or any natural number) and $O_2^-(H_2O)_n$ (n is 0 or any natural number) are generated. $H^+(H_2O)_m$ and $O_2^-(H_2O)_n$ are emitted to the space by means of the fan or the like and adhere to the surface of airborne fungi, followed by chemical reaction. As a result of chemical reaction, $H_2O_2$ or .OH which is an active species is generated. As $H_2O_2$ or .OH exhibits extremely strong activity, airborne fungi in the air are enclosed and inactivated. Here, .OH is a type of active species and represents radical OH.

Positive and negative ions chemically reacts on the surface of cells of the airborne fungi, as shown in expressions (1) to (3), resulting in generation of hydrogen peroxide ($H_2O_2$) or hydroxyl radical (.OH) which is active species. In expressions (1) to (3), m, m', n, and n' represent 0 or any natural number respectively.

In this manner, airborne fungi are destroyed by a decomposition action of the active species. Therefore, the fungi floating in the air can efficiently be inactivated and eliminated.

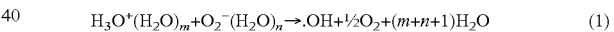  (1)

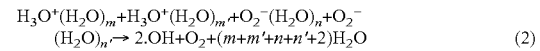  (2)

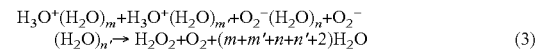  (3)

According to a mechanism described above, an effect to inactivate airborne fungi or the like can be obtained through emission of positive and negative ions shown above.

In addition, according to the expressions (1) to (3) above, the same action can also be achieved on a surface of a toxic substance in the air. Therefore, hydrogen peroxide ($H_2O_2$) or hydroxyl radical (.OH) which is active species oxidizes or decomposes the toxic substance, and transforms a chemical substance such as formaldehyde or ammonia to a harmless substance such as carbon dioxide, water or nitrogen, thereby rendering the toxic substance substantially harmless.

By driving the blower fan, positive and negative ions generated by ion generator 10 can be emitted outside the main unit. An action of such positive and negative ions can inactivate molds and fungi in the air and suppress proliferation thereof.

In addition, the positive and negative ions also serve to inactivate viruses such as coxsackie virus or polio virus, thereby preventing impureness due to introduction of these viruses. Further, as it has been confirmed that the positive and negative ions serve to decompose molecules causing odor, the positive and negative ions can be utilized for deodorization of a space.

Wind was generated toward ion generator 10 by a not-shown fan, and an amount of positive ions and negative ions that arrived at an ion counter positioned approximately 25 cm away from ion generator 10 was measured respectively. At the ion counter, approximately three hundred thousand positive ions and negative ions were measured respectively.

On the other hand, when air conditioning apparatus 100 is in the prediction purification mode, the drive mode of ion generator 10 is set to the clean mode without exception. Here, selection terminal 203c is selected in switch relay 203, while selection terminal 208b is selected in switch relay 208.

Accordingly, the output voltage of AC power supply 201 is subjected to full-wave rectification in a diode bridge constituted of diodes 205a to 205d, then lowered by resistor 204, and applied to capacitor 206. Therefore, an AC impulse voltage of discharge frequency higher than when not in the prediction purification mode (pp value: 3.5 [kV], the number of times of discharge: 240 [times per second], for example) is applied between discharge electrode 12a and induction electrode 12b of ion generator 10, as shown in FIG. 9B.

Here, an amount of ions was measured under the condition described above. As a result, at the ion counter, approximately five hundred thousand positive ions and negative ions per cc were measured respectively. That is, an amount of ions 1.7 times as large as when not in the prediction purification mode was measured.

An operation the same as described above can be achieved also when the connection node of the cathode of diode 205b and the anode of diode 205d is connected to the other end of AC power supply 201 instead of switch relay 203, a switch is connected in series to the anode or the cathode of diode 205c or diode 205d, and the switch is controlled in accordance with the drive mode.

In addition, when ion generator 10 is in the ion control mode, selection terminal 203b is selected in switch relay 203, while selection terminal 208c is selected in switch relay 208.

Figure 9A:
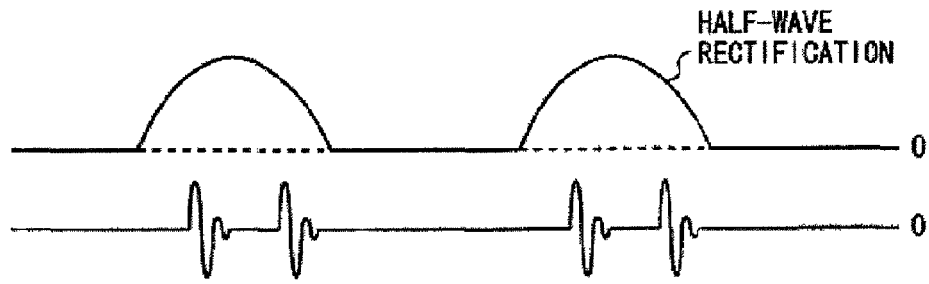
FIG. 9A is a diagram illustrating a voltage pulse output from the voltage application circuit in the first embodiment.
Figure 9B:
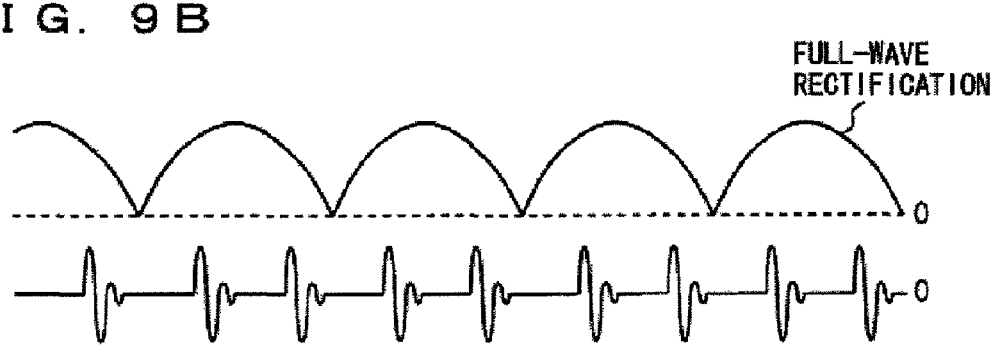
FIG. 9B is another diagram illustrating a voltage pulse output from the voltage application circuit in the first embodiment.

As described above, as half-wave rectification is carried out by diode 209, solely a pulse of the negative voltage among the voltage application pulses shown in FIG. 9A is applied to ion generator 10. Consequently, corona discharge occurs in the vicinity of ion generator 10, and the ambient air is ionized. Here, as solely the negative voltage is applied, $O_2^-(H_2O)_n$ which is negative ion is generated.

<First Variation of Voltage Application Circuit>

Figure 10:
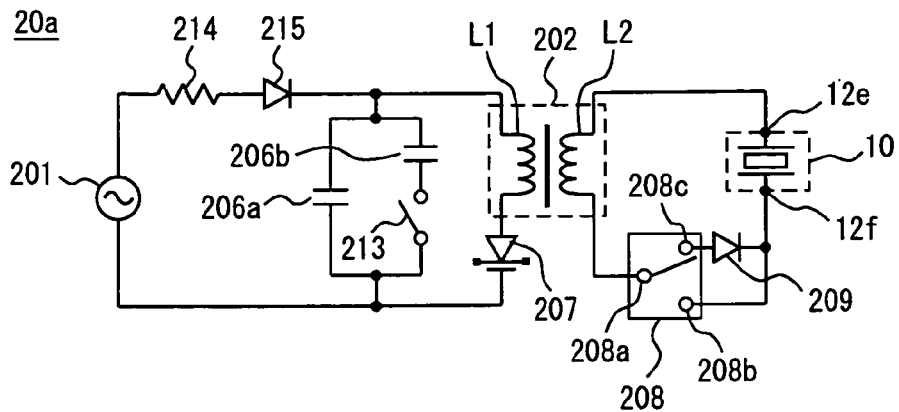
FIG. 10 is a circuit diagram of a voltage application circuit in a variation of the first embodiment.

FIG. 10 is a circuit diagram of a variation of the voltage application circuit. Referring to FIG. 10, the voltage application circuit here is different from voltage application circuit 20 in FIG. 8 in a circuit configuration between AC power supply 201 and primary coil L1 in switching transformer 202. As other circuits are the same as in the first embodiment, description thereof will not repeated. One end of AC power supply 201 is connected to one end of a resistor 214, while the other end of resistor 214 is connected the anode of a capacitor 215. The other end of AC power supply 201 is connected to the cathode of SIDAC (R) 207, one end of capacitor 106a, and one end of a switch 213. The cathode of a diode 215 is connected to one ends of capacitors 206a, 206b and primary coil L1. The other end of capacitor 206b is connected to the other end of switch 213.

In a voltage application circuit 20a in the variation configured in the above-described manner, when air conditioning apparatus 100 is not in the prediction purification mode, relay 213 closes. The output voltage of AC power supply 201 is subjected to half-wave rectification in diode 215, and thereafter applied to capacitors 206a and 206b. When capacitors 206a and 206b are charged and voltages across the capacitors attain a prescribed threshold value, SIDAC (R) 207 attains an on state and the charged voltages of capacitors 206a and 206b are discharged. Accordingly, a current flows through primary coil L1 in transformer 202 to transmit energy to secondary coil L2, whereby a pulse voltage is applied to ion generator 10. Immediately thereafter, SIDAC (R) 207 attains an off state and charge of capacitors 206a and 206b is started again.

On the other hand, when air conditioning apparatus 100 is in the prediction purification mode, relay 213 opens. The output voltage of AC power supply 201 is subjected to half-wave rectification in diode 215, and applied solely to capacitor 206a. When capacitor 206a is charged and a voltage across the capacitor attains a prescribed threshold value, SIDAC (R) 207 attains an on state and the charged voltage of capacitor 206a is discharged. Accordingly, a current flows through primary coil L1 in transformer 202 to transmit energy to secondary coil L2, whereby a pulse voltage is applied to ion generator 10. Immediately thereafter, SIDAC (R) 207 attains an off state and charge of capacitor 206a is started again.

When switch 213 is open, the voltage applied to SIDAC (R) 207 attains the threshold value earlier than when it is closed. Therefore, the discharge frequency of the voltage pulse applied to ion generator 10 becomes higher when switch 213 is open than when it is closed. As the discharge frequency of the pulse applied to ion generator 10 is higher, an amount of generated ions increases. Therefore, solely by switching switch 213, an amount of ions generated from ion generator 10 can be switched.

Figure 11A:
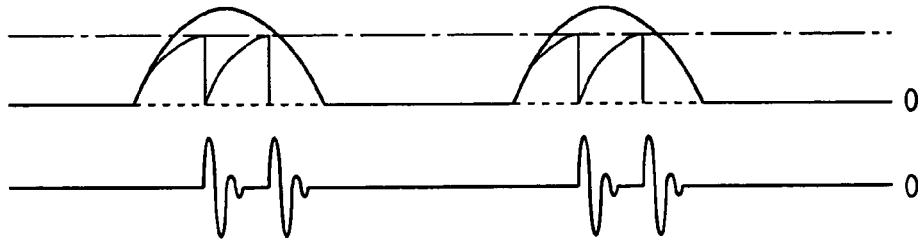
FIG. 11A is a diagram illustrating a voltage pulse output from the voltage application circuit in the variation.
Figure 11B:
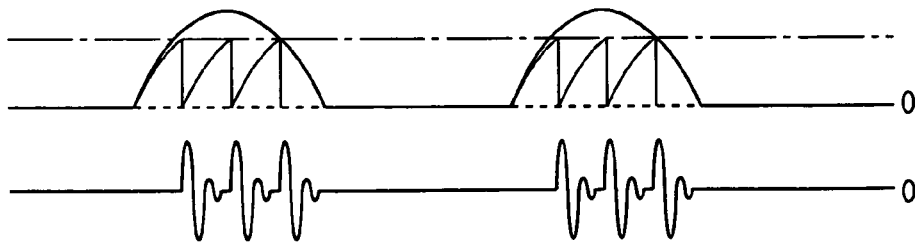
FIG. 11B is another diagram illustrating a voltage pulse output from the voltage application circuit in the variation.

FIGS. 11A and 11B show waveforms of voltages output from voltage application circuit 20a in the variation. FIG. 11A shows a waveform when switch 213 is closed, and illustrates a waveform of a voltage that has been subjected to half-wave rectification in diode 215 and a waveform of a voltage pulse applied to ion generator 10. FIG. 11B illustrates a waveform of a voltage that has been subjected to half-wave rectification when switch 213 is open and a waveform of a voltage pulse applied to ion generator 10

In voltage application circuit 20 described above, half-wave rectification and full-wave rectification have been switched by switching switch 203. Though solely an example of half-wave rectification has been described with regard to voltage application circuit 20a in the variation, switching between full-wave rectification and half-wave rectification may be employed. In such a case, when the voltage pulse of low discharge frequency is applied to ion generator 10, the voltage that has been subjected to half-wave rectification is used and switch 213 is closed. Meanwhile, when a voltage pulse of high discharge frequency is applied to ion generator 10, full-wave rectification is used and switch 213 is opened.

<Second Variation of Ion Generator and Voltage Application Circuit>

FIGS. 12A and 12B show variations of the ion generator in the first embodiment. Referring to FIGS. 12A and 12B, an ion generator 10A in this variation is different from ion generator 10 described above in that it includes a first discharge portion 21 constituted of a discharge electrode 21a and an induction electrode 21b, and a second discharge portion 22 constituted of a discharge electrode 22a and an induction electrode 22b. In other words, ion generator 10A in this variation is different in including two discharge portions 21 and 22.

In ion generator 10A in this variation, induction electrodes 21b and 22b are formed on a surface of lower dielectric 11b, while discharge electrodes 21a and 22a are formed on a surface of upper dielectric 11a. The surface of upper dielectric 11a is covered with coating layer 13. In addition, upper dielectric 11a is stacked on the surface of lower dielectric 11b where induction electrodes 21b and 22b are formed. Discharge electrode 21a and induction electrode 21b in first discharge portion 21 are arranged in positions opposing to each other, while discharge electrode 22a and induction electrode 22b in second discharge portion 22 are arranged in positions opposing to each other.

In the first discharge portion, connection terminal 21e of discharge electrode 21a is connected to discharge electrode contact 21e, which is connected to a voltage application circuit 20B via a lead. In addition, connection terminal 21d of induction electrode 21b is connected to induction electrode contact 21f, which is connected to voltage application circuit 20B via a lead.

Similarly, in second discharge portion 22, connection terminal 22c of discharge electrode 22a is connected to discharge electrode contact 22e, which is connected to voltage application circuit 20B via a lead. In addition, connection terminal 22d of induction electrode 22b is connected to induction electrode contact 22f, which is connected to voltage application circuit 20B via a lead.

Figure 13:
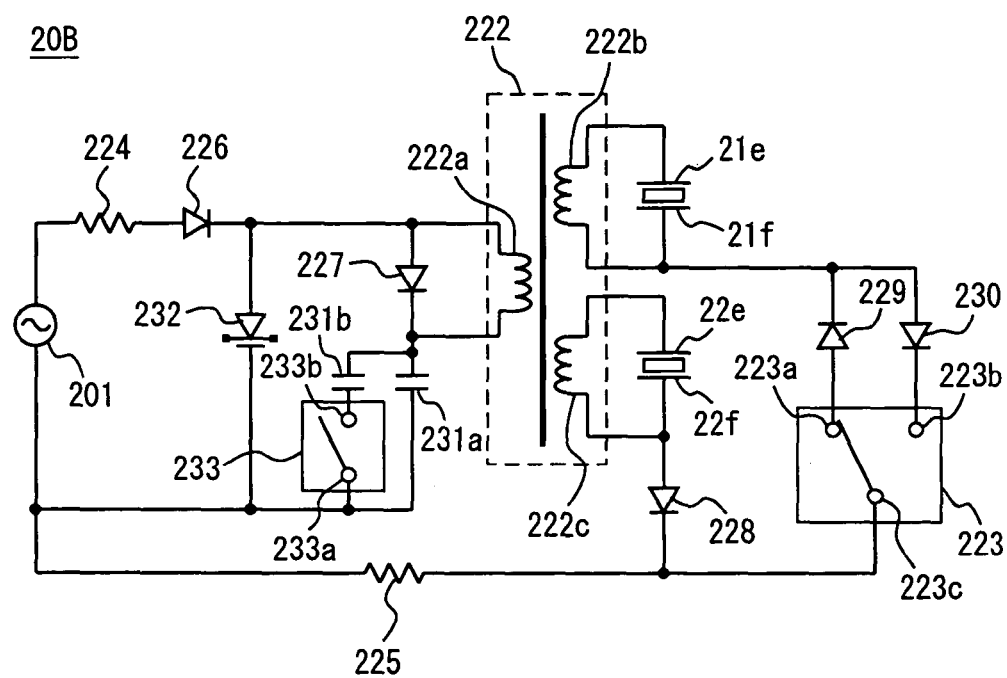
FIG. 13 is a circuit diagram of a voltage application circuit connected to the ion generator in the variation.

FIG. 13 is a circuit diagram of voltage application circuit 20B connected to ion generator 10A in the variation. Referring to FIG. 13, voltage application circuit 20B includes AC power supply 201, a transformer 222, a switch relay 233, resistors 224, 225, diodes 226 to 230, capacitors 231a, 231b, and an SIDAC (R) 232.

One end of AC power supply 201 is connected to the anode of diode 226 via resistor 224. The cathode of diode 226 is connected to one end of a first coil 222a implementing a primary side of transformer 222, the anode of diode 227, and the anode of SIDAC (R) 232. The other end of first coil 222a is connected to the cathode of diode 227, of which connection node is connected to one ends of capacitors 231a and 231b. The cathode of SIDAC (R) 232, the other end of capacitor 231a, and one end 233a of switch 233 are connected to one another, of which connection node is connected to the other end of AC power supply 201. The other end 233b of switch 233 is connected to the other end of capacitor 231b.

One end of a second coil 222b implementing a secondary side of transformer 222 is connected to discharge electrode contact 21e of first discharge portion 21, while the other end of second coil 222b is connected to induction electrode contact 21f of first discharge portion 21, the cathode of diode 229, and the anode of diode 230. The anode of diode 229 is connected to one selection terminal 223a of switch relay 223, and the cathode of diode 230 is connected to the other selection terminal 223b of switch relay 223. One end of a third coil 222c implementing a secondary side of transformer 222 is connected to discharge electrode contact 22e of second discharge portion 22, while the other end of third coil 222c is connected to induction electrode contact 22f of second discharge portion 22 and the anode of diode 228. A common terminal 223c of switch relay 223 is connected to the cathode of diode 228, of which connection node is connected to the other end of AC power supply 201 via resistor 225.

In voltage application circuit 20B configured in the above-described manner, when air conditioning apparatus 100 is not in the prediction purification mode and when the drive mode in ion generator 10 is set to the clean mode, switch 233 closes and selection terminal 223a is selected in switch relay 223. Here, a positive DC impulse voltage is applied between discharge electrode 21a and induction electrode 21b in first discharge portion 21, while a negative DC impulse voltage is applied between discharge electrode 22a and induction electrode contact 22b in second discharge portion 22. By application of such voltages, corona discharge occurs in the vicinity of first discharge portion 21 and second discharge portion 22, and the ambient air is ionized. Here, $H^+(H_2O)_m$ which is a positive ion is generated in the vicinity of first discharge portion 21 to which the positive DC impulse has been applied, whereas $O_2^-(H_2O)_n$ which is a negative ion is generated in the vicinity of second discharge portion 22 to which the negative DC impulse has been applied (m, n are 0 or any natural number).

In this manner, when selective terminal 223a is selected in switch relay 223, substantially the same amount of positive ions and negative ions can be generated from first discharge portion 21 and second discharge portion 22 respectively. Therefore, positive and negative ions are caused to adhere to floating fungi or the like in the air, so that floating fungi can be eliminated with decomposition action of generated hydrogen peroxide ($H_2O_2$) and/or hydroxyl radical (.OH) which is active species.

On the other hand, when air conditioning apparatus 100 operates in the prediction purification mode, switch 233 is opened and selection terminal 223a is selected in switch relay 223. In this case, solely capacitor 231a is charged. Therefore, a time period until the voltage applied to SIDAC (R) 232 attains the prescribed threshold value is shortened. Accordingly, discharge frequencies of the positive DC impulse voltage applied to first discharge portion 21 and the negative DC impulse voltage applied to second discharge portion 22 are increased. In this manner, a larger amount of positive ions is generated in first discharge portion 21, and a larger amount of negative ions is generated in second discharge portion 22.

When air conditioning apparatus 100 does not operate in the prediction purification mode and when the drive mode of ion generator 10 is set to the ion control mode, switch 233 is closed and selection terminal 22ba is selected in switch relay 223.

In such a case, the negative DC impulse voltage is applied to both first discharge portion 21 and second discharge portion 22. When such a negative DC impulse voltage is applied, $O_2^-(H_2O)_n$ which is a negative ion (n is 0 or any natural number) is generated in the vicinity of both first discharge portion B21 and second discharge portion 22.

As described above, when selection terminal 223b is selected in switch relay 223, solely negative ions can be generated from both first discharge portion 21 and second discharge portion 22. Therefore, ion balance can be adjusted so as to create a state in which negative ions are dominant, thereby enhancing relaxation effect.

A degree of impureness will now be described. FIG. 14 shows an example of a degree of impureness evaluation table used in air conditioning apparatus 100 in the first embodiment. The degree of impureness evaluation table is stored in advance in a read-only memory (ROM) in control unit 150 in air conditioning apparatus 100.

Referring to FIG. 14, the degree of impureness evaluation table associates odor sensor output levels, dust sensor output levels and results of addition of values from both sensors with the degree of impureness for storage. In the present embodiment, output levels of odor sensor 154 ranges from 0 to 3, while output levels of dust sensor 153 ranges from 0 to 3. That is, an amount of odor and dust is expressed and output in 4 levels. As the value for odor sensor output level becomes larger, it indicates that an amount of substances in the air causing the odor is larger. Meanwhile, an amount of dust in the air is larger, as the value for dust sensor output level becomes larger. The addition result represents the sum of the odor sensor output level and the dust sensor output level. The addition result ranges from 0 to 6.

The degree of impureness is associated with the odor sensor output level and the dust sensor output level. Even when the addition results are the same, the degree of impureness may be different. For example, when the odor sensor output level attains 1 and the dust sensor output level attains 2, the addition result is 3 and this example is associated with the degree of impureness of 1. On the other hand, when the odor sensor output level attains 3 and the dust sensor output level attains 0, this example is associated with the degree of impureness of 2 in spite of the addition result of 3. This is because the odor sensor output level attains 3, which indicates that a largest amount of substances causing odor is present. In such a case, the degree of impureness is determined as 2, not 1.

In the drawing, a color on the clean sign indicator light corresponds to the degree of impureness. That is, when the degree of impureness is 0, clean sign indicator light 114 illuminates in green. When the degree of impureness is 1, clean sign indicator light 114 illuminates in orange. When the degree of impureness is 2, clean sign indicator light 114 illuminates in red. The undetected mode in the drawing refers to a mode set until the output levels of odor sensor 154 and dust sensor 153 are stabilized. During such a time period, the degree of impureness is not determined, and accordingly, it is referred to as "undetected mode". Here, clean sign indicator light 114 illuminates in the order of green, orange and red, and thereafter illuminates in the order of red, orange and green, which will be repeated. Clean sign indicator light 114 illuminates sequentially in different colors, so that the user can be notified that the degree of impureness is not yet evaluated.

Though the degree of impureness has ranged in 3 levels from 0 to 2 here, the range is not limited to such an example. A larger or smaller number of levels may be set, and two levels may be set, for example. In addition, though the degree of impureness has been detected based on the output values from two sensors of odor sensor 154 and dust sensor 153 in the present embodiment, any one sensor output may be used to detect the degree of impureness.

Figure 15:
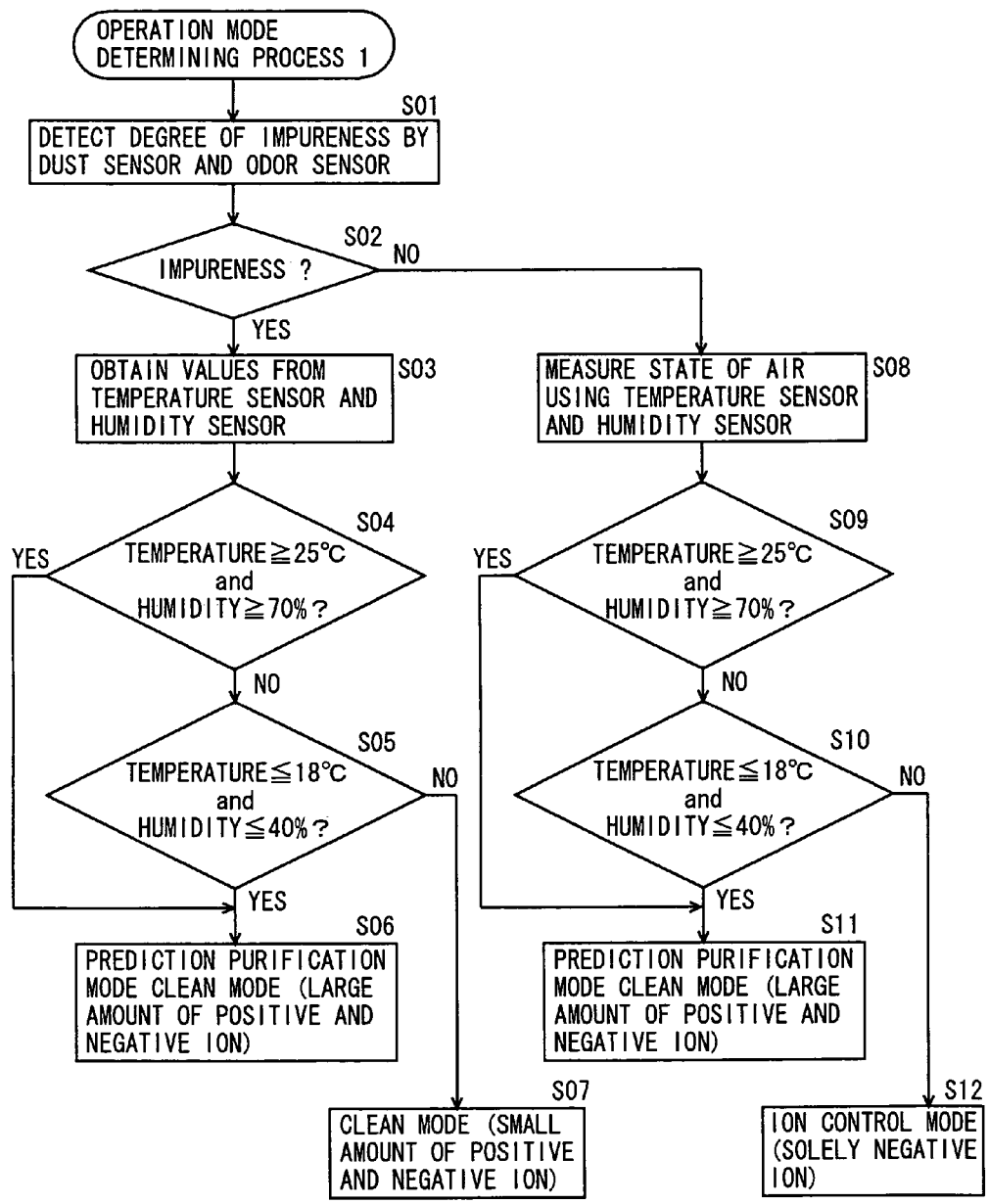
FIG. 15 is a flowchart illustrating a flow of an operation mode determining process executed in the air conditioning apparatus in the first embodiment.

FIG. 15 is a flowchart illustrating a flow of an operation mode determining process executed in air conditioning apparatus 100 in the first embodiment. The operation mode determining process is executed in control unit 150 of air conditioning apparatus 100. Referring to FIG. 15, in the operation mode determining process, the degree of impureness is detected based on output levels from dust sensor 153 and odor sensor 154 (step S01), using the degree of impureness evaluation table described above. Then, based on the detected degree of impureness, whether or not the air in the room is impure (step S02). When the air in the room is determined as impure, the process proceeds to step S03, and otherwise the process proceeds to step S08. Here, when the degree of impureness detected at step S01 attains at least 1, determination as impure is made at step S02.

At next step S03, output values of temperature sensor 151 and humidity sensor 152 are obtained. At step S04, whether or not the obtained output values of the temperature sensor and the humidity sensor are at least 25° C. and at least 70% respectively is determined. When the output values from the temperature sensor and the humidity sensor satisfy the condition above, the process proceeds to step S06, and otherwise the process proceeds to step S05. At step S04, whether or not the air in the room is in a state in which molds are likely to proliferate is determined. Therefore, the threshold values of the temperature and the humidity are not limited to 25° C. and 70% respectively, and any value close to those may be accepted.

At step S05, whether or not the output values of the temperature sensor and the humidity sensor both obtained at step S03 are at most 18° C. and at most 40% respectively is determined. When the output values from the temperature sensor and the humidity sensor satisfy the condition above, the process proceeds to step S06, and otherwise the process proceeds to step S07. At step S05, whether or not the air in the room is in a state in which influenza viruses are likely to proliferate is determined. Therefore, the threshold values of the temperature and the humidity are not limited to 18° C. and 40% respectively, and any value close to those may be accepted.

At step S06, the operation mode of air conditioning apparatus 100 is set to the prediction purification mode and the clean mode. Accordingly, a large amount of positive and negative ions is generated from ion generator 10. Here, on display portion 103, prediction purification indicator light 113 illuminates and cluster ion indicator light 115 illuminates in blue.

On the other hand, at step S07, the prediction purification mode is not set and solely the clean mode is set. Accordingly, a normal amount of positive and negative ions is generated from ion generator 10, which amount is smaller than in the operation mode set at step S06. Here, on display portion 103, prediction purification indicator light 113 turns off and cluster ion indicator light 115 illuminates in blue.

When the air in the room has been determined as clean at step S02, the process proceeds to step S08. At step S08, output values from temperature sensor 151 and humidity sensor 152 are obtained. The process in this step is similar to that in step S03.

The process in step S09 is similar to that in step S04. That is, whether or not the temperature is at least 25° C. and the humidity is at least 70% is determined, using the output values from temperature sensor 151 and humidity sensor 152 obtained at step S08. When the temperature and the humidity satisfy the condition, the process proceeds to step S11, and otherwise the process proceeds to step S10.

The process in step S10 is similar to that in step S05 described above. When the conditions of the temperature of at most 18° C. and the humidity of at most 40% are satisfied, the process proceeds to step S11, and otherwise the process proceeds to step S12.

At step S11, the operation mode of air conditioning apparatus 100 is set to the prediction purification mode and also to the clean mode. This operation mode is the same as in step S06. In such an example, the air in the room is either in a state in which molds are likely to proliferate or a state in which influenza viruses are likely to proliferate. Here, positive and negative ions are generated from ion generator 10, and an amount thereof is increased as compared with the normal amount.

On the other hand, at step S12, the operation mode of air conditioning apparatus 100 is set to the ion control mode. When the process proceeds to step S12, the air in the room is clean and not in the state in which molds or influenza viruses are likely to proliferate. As a probability of presence of molds or influenza viruses in the air in the room is low, ion generator 10 generates not positive and negative ions but negative ions in an amount larger than positive ions. Here, on display portion 103, prediction purification indicator light 113 turns off and cluster ion indicator light 115 illuminates in green.

Control unit 150 controls voltage driving circuit 20 in accordance with respective operation modes at steps S06, S07, S11, and S12. Controlled by control unit 150, voltage driving circuit 20 applies a driving voltage determined in accordance with the operation mode to ion generator 10.

Ion generator 10 generates a large amount of ions when the voltage pulse of high discharge frequency is applied thereto. In addition, an amount of positive and negative ions generated from ion generator 10 can be controlled also by varying a duty ratio of the applied voltage pulse. Under the condition that the cycle of the applied voltage pulse is constant, an amount of generated ions from ion generator 10 is larger when the duty is set to 100% than when it is set to 50%. Voltage driving circuit 20 can control an amount of positive and negative ions generated from ion generator 10 by varying the duty.

FIG. 16 shows a relation between the operation mode of air conditioning apparatus 100 and a fan motor output and a voltage applied to ion generator 10 in the first embodiment. Here, the voltage applied to ion generator 10 when the duty is varied is shown. Referring to FIG. 16, • represents examples in which the operation mode is set to the prediction purification mode, while x represents examples in which the operation mode is not set to the prediction purification mode. In addition, a field of the ion mode includes the clean mode and the ion control mode. That is, in air conditioning apparatus 100 in the present embodiment, the operation mode includes three modes: the clean mode not in the prediction purification mode; the clean mode in the prediction purification mode; and the ion control mode not in the prediction purification mode.

When the operation mode is set to the prediction purification mode, the air in the room may be in the first state in which molds are likely to proliferate or in the second state in which influenza viruses are likely to proliferate. The clean mode is different from the ion control mode in that positive and negative ions are generated from ion generator 10 in the clean mode and that negative ions are generated from ion generator 10 in an amount larger than that of positive ions in the ion control mode. If the operation mode is set not only to the clean mode but also to the prediction purification mode, an amount of generated positive and negative ions is larger than when the prediction purification mode is not set.

It is noted that an amount of ions generated from ion generator 10 in the present embodiment refers to a ratio of positive ions to negative ions in the air, and relates to the fan motor output. Here, the fan motor output is indicated by the volume of air, which is categorized in 6 levels from fan level 1 to 6. Fan speed is larger at fan level 6 than at fan level 1.

When an applied voltage duty increases, generated discharge noise also becomes greater. Accordingly, when the fan motor output is small and wind noise is small, the discharge noise from the ion generator is preferably small. Therefore, by changing the applied voltage duty in accordance with the fan motor output, silent operation of an entire product can be realized.

When the wind speed is low, an amount of air flowing over ion generator 10 becomes smaller. Accordingly, even if an actual amount of ionized air is small in ion generator 10, ion concentration becomes higher. Therefore, the ion concentration at fan level 1 and duty 20% is higher than that at fan level 6 and duty 50%. That is, the ion concentration at fan level 1 and duty 20% in the prediction purification mode is higher than that at fan level 6 and duty 50% when not in the prediction purification mode but in the clean mode. Thus, an amount of generated ions in the prediction purification mode is larger than that when not in the prediction purification mode.

When the wind speed is low, the wind noise is also small. In order to lower overall operation noise, the discharge noise from the ion generator and the voltage duty are preferably small. In contrast, when the wind speed is high, the wind noise is also great. Therefore, even if the discharge noise from the ion generator is great, it does not considerably affect the overall operation noise. Therefore, by setting duty 100% at fan level 5 or 6, quietness and desired ion concentration can be realized without much affecting the overall operation noise.

FIG. 16 also shows a manner of indication on cluster ion indicator light 115 in accordance with respective modes. Specifically, in the clean mode not in the prediction purification mode, cluster ion indicator light 115 illuminates in blue. In addition, in the clean mode and the prediction purification mode, cluster ion indicator light 115 slowly repeats flashing in blue in a cycle of 5 seconds. When flashing of cluster ion indicator light 115 in blue is observed, the operation is in the prediction purification mode.

When air conditioning apparatus 100 is not in the prediction purification mode but in the ion control mode, cluster ion indicator light 115 illuminates in green.

As described above, in air conditioning apparatus 100 in the present embodiment, positive and negative ions in an amount larger than normal are generated when the air in the room is in the state in which molds are likely to proliferate (YES at step S04 or S09) or in the state in which influenza viruses are likely to proliferate (YES at step S05 or S10). Therefore, in the state in which fungi such as molds or influenza viruses are likely to proliferate, a large amount of positive and negative ions is generated so as to enhance an effect to kill fungi such as molds and influenza viruses.

In addition, in air conditioning apparatus 100 in the present embodiment, ion generator 10 generates a normal amount of positive and negative ions, when the air in the room is not in the state in which molds are likely to proliferate (NO at step S04) but in the state in which influenza viruses are less likely to proliferate (NO at step S05). Therefore, even when the air in the room is not in the state in which airborne fungi are likely to proliferate, airborne fungi can be killed. Namely, the airborne fungi can further be killed. In addition, since the voltage pulse of low discharge frequency or the pulse of small duty is applied to ion generator 10, power consumption is reduced and the discharge noise is suppressed.

Moreover, when the air in the room is clean (NO at step S02) and when the air in the room is in the state in which molds are unlikely to proliferate (NO at step S09) and in the state in which influenza viruses are unlikely to proliferate (NO at step S11), ion generator 10 is set to the ion control mode in which negative ions in an amount larger than that of positive ions are generated. Accordingly, as the concentration of negative ions is increased in the room, refreshing effect is achieved. In this manner, when the air in the room is clean and in an environment in which airborne fungi are less likely to proliferate, an environment comfortable for humans can be created.

In addition, the operation mode of air conditioning apparatus 100 in the present embodiment is set to the clean mode (step S06 or S07) when the air in the room is impure (YES at step S02). Accordingly, positive and negative ions are generated from ion generator 10. When the air in the room is impure, it is probable that airborne fungi are contained. Therefore, by generating both positive and negative ions, airborne fungi in the air can efficiently be killed.

When the air in the room is impure (YES at step S02) and in the state in which molds are likely to proliferate (YES at step S04) or in the state in which influenza viruses are likely to proliferate (YES at step S05), an amount of generated positive and negative ions is increased. Accordingly, when the room is in the state in which molds are likely to proliferate or in the state in which influenza viruses are likely to proliferate, an amount of generated positive and negative ions is increased, so as to efficiently kill airborne fungi. Moreover, as the voltage pulse of high discharge frequency or of large duty is applied to ion generator 10 solely in the prescribed state, it is not necessary to always apply the voltage pulse of high discharge frequency or of large duty. That is, power consumption in ion generator 10 can be reduced. Further, when the voltage pulse of high discharge frequency is applied, ion generator 10 produces noise greater than when the voltage pulse of low discharge frequency is applied. As described above, since the voltage pulse of high discharge frequency is applied solely in the prescribed state, the noise can be minimized.

When the voltage pulse of high discharge frequency or of large duty is applied, ion generator 10 experiences faster deterioration than when the voltage pulse of low discharge frequency or of small duty is applied. Accordingly, since the voltage pulse of high discharge frequency or of large duty is not always applied to ion generator 10, ion generator 10 can be used for a long period of time.

Though air conditioning apparatus 100 with ion generator 10 has been described in the present embodiment, ion generator 10 may be applied to a dehumidifier attaining a dehumidifying function. The dehumidifier carries out dehumidification when the humidity in the room increases, so as to maintain the humidity in the room to a prescribed level. Accordingly, if the humidity in the room is adjusted so as to attain the state in which molds are less likely to proliferate or so as to maintain the humidity at which influenza viruses are less likely to proliferate, effects from dehumidification of the air by means of the dehumidifier and the positive and negative ions generated by ion generator 10 are combined to attain the state of the air in the room in which molds are less likely to proliferate or the state in which influenza viruses are less likely to proliferate. Even if the room is in the state in which molds are likely to proliferate, proliferation thereof can be prevented by dehumidification by means of the dehumidifier, and molds can efficiently be killed by virtue of the positive and negative ions generated by ion generator 10.

Note that a humidifier attaining a humidifying function may be employed instead of the dehumidifier. Unlike the dehumidifier, the humidifier increases the humidity in the room. Therefore, when the humidity in the room is lowered and the room is in the state in which influenza viruses are likely to proliferate, humidification by means of the humidifier is carried out and an environment in which influenza viruses are less likely to proliferate is achieved. Thus, proliferation of the virus is prevented, and influenza viruses can efficiently be killed by virtue of the positive and negative ions generated by ion generator 10.

Furthermore, ion generator 10 may be applied to an air conditioner attaining a function to cool or warm the air in the room. The air conditioner can warm or cool the air in the room, so as to set a temperature at which molds are less likely to proliferate or so as to adjust the temperature in the room to a level at which influenza viruses are less likely to proliferate. Therefore, even if the room is in the state in which molds or viruses are likely to proliferate, the temperature is adjusted by cooling/warming function, thereby attaining an environment in which molds or influenza viruses are less likely to proliferate. Thus, proliferation of the molds and viruses is prevented, and the molds and the influenza viruses can efficiently be killed by virtue of the positive and negative ions generated by ion generator 10.

In addition, ion generator 10 may be applied to an air conditioner implemented by a combination of a dehumidifier, a humidifier, a heater, and a cooler.

In the present embodiment, the prescribed state has been defined as the state of the air in the room determined by the temperature and the humidity, including the first state determined by the temperature and the humidity at which molds are likely to proliferate and the second state determined by the temperature and the humidity at which viruses are likely to proliferate. In addition, the first state has been defined as the state of the temperature and the humidity of at least 25° C. and at least 70% respectively, while the second state has been defined as the state of the temperature and the humidity of at most 18° C. and at most 40% respectively. The first and the second states, however, are not limited to such an example. The first state may be any state determined by the temperature and the humidity at which molds are likely to proliferate, and the second state may be any state determined by the temperature and the humidity at which viruses such as influenza viruses are likely to proliferate.

FIG. 17 shows one example of the prescribed state. Referring to FIG. 17, the ordinate represents the temperature, while the abscissa represents the humidity, so as to show a region determined by the temperature and the humidity. The first state includes a region defined by the temperature of at least 13° C. and the humidity of at least 70%. The second state includes a region defined by the temperature of at most 13° C. and the humidity from at least 0% to at most 100%, a region defined by the temperature from at least 13° C. to at most 24° C. and the humidity from at least 0% to at most 40%, and a region defined by the temperature from at least 24° C. to at most 34° C. and the humidity from at least 0% to at most 25%.

Accordingly, the first state includes a region defined by the temperature of at least 25° C. (first temperature) and the humidity of at least 70% (first humidity). In addition, the second state includes a region defined by the temperature of at most 18° C. (second temperature) and the humidity of at most 40% (second humidity). The second temperature is lower than the first temperature, while the second humidity is lower than the first humidity.

When the prescribed state shown in FIG. 17 is used, in the operation mode determining process shown in FIG. 15, whether or not the air in the room determined by the temperature and the humidity is in the first state is determined at step S04 or S09. When the air in the room is in the first state, determination as "true" is made, and otherwise determination as "false" is made. In addition, whether or not the air in the room determined by the temperature and the humidity is in the second state is determined at step S05 or S10. When the air in the room is in the second state, determination as "true" is made, and otherwise determination as "false" is made.

Second Embodiment

In air conditioning apparatus 100 in the first embodiment described above, when the operation mode determining process shown in FIG. 15 is executed, whether or not the prediction purification mode is to be set has automatically been determined. In an air conditioning apparatus 100A in the second embodiment, however, whether or not the operation mode is set to the prediction purification mode can be selected by the user. Accordingly, air conditioning apparatus 100A in the second embodiment includes a prediction purification mode operation switch for switching the operation mode to the prediction purification mode. Moreover, air conditioning apparatus 100A in the second embodiment attains a function to notify the user that the air in the room is in a state suitable for operation in the prediction purification mode. In the following, differences from air conditioning apparatus 100 in the first embodiment will be described.

Figure 18A:
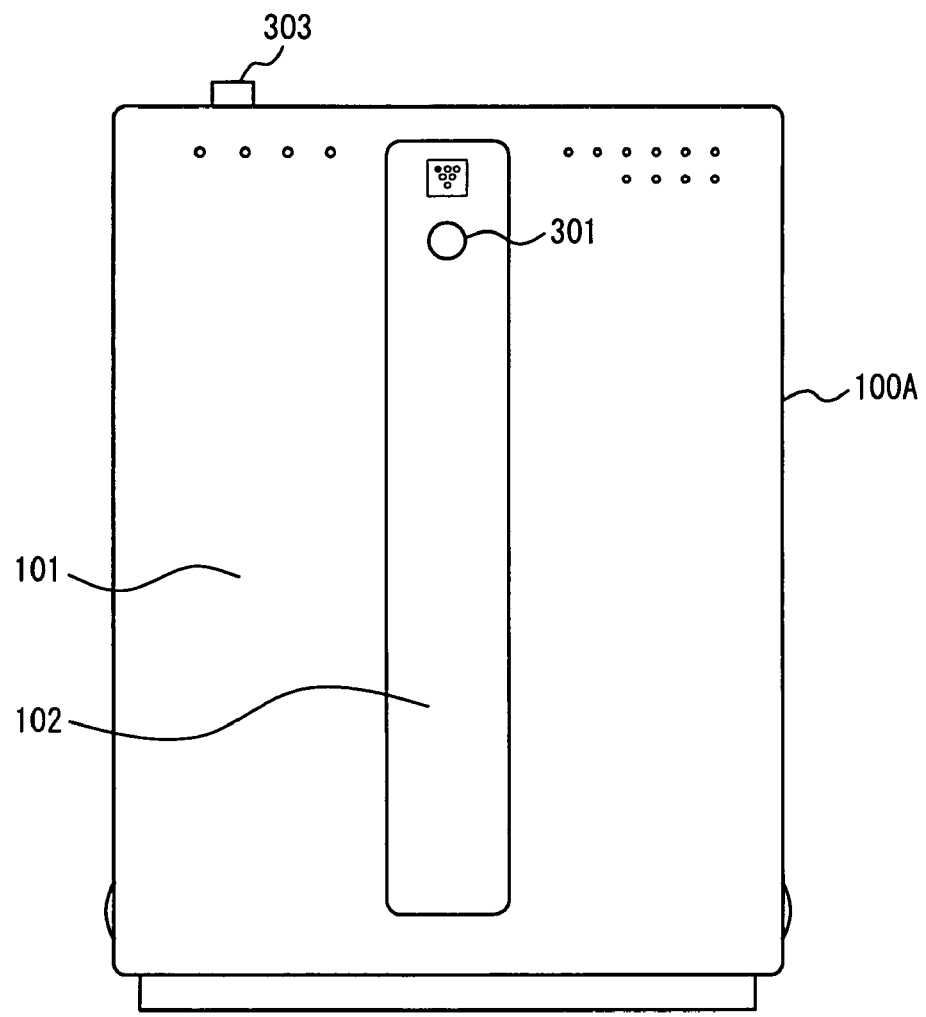
FIG. 18A is a front view showing appearance of an air conditioning apparatus in a second embodiment.
Figure 18B:
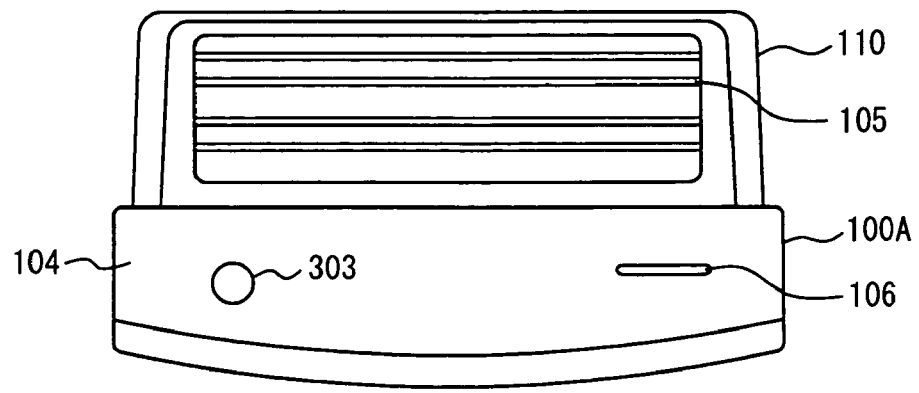
FIG. 18B is a plan view showing appearance of the air conditioning apparatus in the second embodiment.

FIGS. 18A and 18B shows appearance of air conditioning apparatus 100A in the second embodiment. Second air conditioning apparatus 100A includes a notification light 301 in an upper portion of central panel 102 and a prediction purification mode operation switch 303 on top panel 104.

Notification light 301 illuminates or flashes when the air in the room is in the first state or in the second state described above. With this light, the user can be notified that the air in the room is in the first state or in the second state. Note that notification light 301 may be a display device such as a liquid crystal display device, the cathode ray tube (CRT) or electroluminescence, or a sound output device such as a speaker or a buzzer. Alternatively, a combination of the display device and the sound output device may be employed. When the display device is used, a message such as "molds are likely to proliferate" or "viruses are likely to proliferate" may be displayed in order to indicate that the air in the room is in the first state or in the second state. Moreover, a message such as "press the prediction purification mode operation switch" may be displayed in order to urge manipulation of the prediction purification mode operation switch. When the sound output device is used, the message described above may be output as sound, or alternatively an alarm (including melody) may be output. Notification light 301 may be provided also in remote controller 130, in addition to in air conditioning apparatus 100A.

Prediction purification mode operation switch 303 serves as an input switch for accepting manipulation by the user when the air in the room is in the first state or in the second state. When manipulation by the user is accepted, air conditioning apparatus 100A starts operation in the prediction purification mode. Prediction purification mode operation switch 303 may be provided also in remote controller 130, in addition to in air conditioning apparatus 100A.

Figure 19:
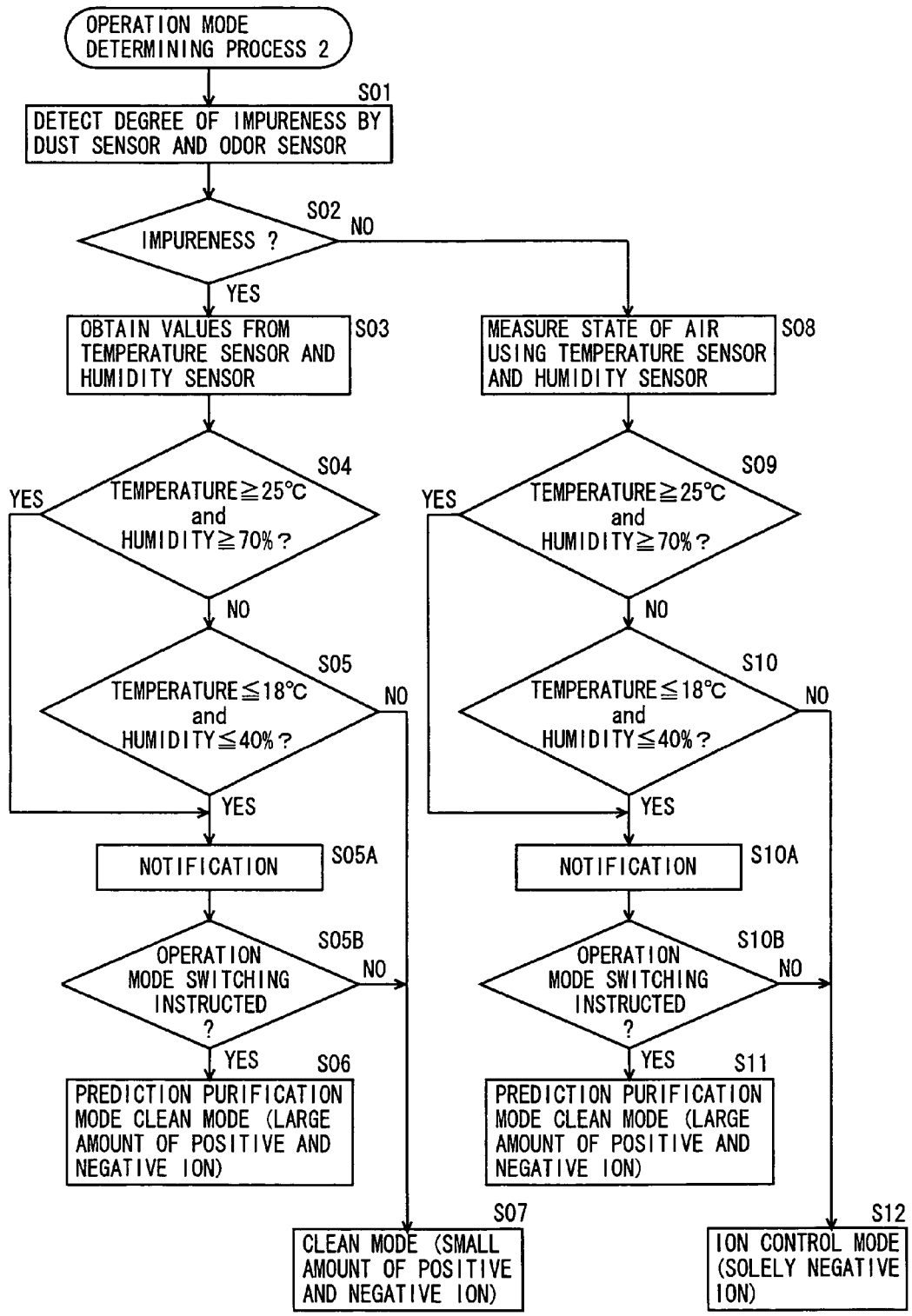
FIG. 19 is a flowchart illustrating a flow of an operation mode determining process executed in the air conditioning apparatus in the second embodiment.

FIG. 19 is a flowchart illustrating a flow of an operation mode determining process executed in air conditioning apparatus 100A in the second embodiment. The operation mode determining process is executed in control unit 150 of air conditioning apparatus 100A. The operation mode determining process shown in FIG. 19 is different from that executed in air conditioning apparatus 100 in the first embodiment shown in FIG. 15 in that new steps S05A and S05B are added between step S05 and step S06 and that new steps S10A and S10B are added between step S10 and step S11. As the processes from step S01 to step S05 and from step S08 to step S10 are the same as described with reference to FIG. 15, description thereof will not be repeated.

If determination as YES is made at step S04 or S05, the process proceeds to step S05A. In other words, the process proceeds to step S05A when the state of the air in the room determined by the temperature and the humidity is in the first state or in the second state.

At step S05A, notification light 301 illuminates or flashes. In this manner, the user is notified that the air in the room is in the first state or in the second state.

At next step S05B, whether or not prediction purification mode operation switch 303 has been manipulated by the user is determined. If manipulation by the user is detected, the process proceeds to step S06, and otherwise the process proceeds to step S07.

On the other hand, if determination as YES is made at step S09 or S10, the process proceeds to step S10A. In other words, the process proceeds to step S10A when the state of the air in the room determined by the temperature and the humidity is in the first state or in the second state.

The process at step S10A is the same as that at step S05A. That is, notification light 301 illuminates or flashes. In this manner, the user is notified that the air in the room is in the first state or in the second state.

Next step S10B is the same as that at step S05B. That is, whether or not prediction purification mode operation switch 303 has been manipulated by the user is determined. If manipulation by the user is detected, the process proceeds to step S11, and otherwise the process proceeds to step S12.

In this manner, in the air conditioning apparatus in the second embodiment, notification light 301 illuminates or flashes. Thus, the user is notified that the air in the room is in the first state or in the second state. Then, after an instruction by the user through prediction purification mode operation switch 303, the operation mode is set to the prediction purification mode and also to the clean mode. When the operation mode is set to the prediction purification mode, positive and negative ions in an amount larger than normal are generated from ion generator 10. In addition, on display portion 103, prediction purification indicator light 113 illuminates and cluster ion indicator light 115 illuminates in blue.

As described above, in air conditioning apparatus 100A in the second embodiment, when the air in the room is in the first state or in the second state, the operation mode is set to the prediction purification mode and the clean mode after the instruction by the user arrives. When the operation mode of air conditioning apparatus 100A is set to the prediction purification mode and the clean mode, power consumption by ion generator 10 is larger than in other operation mode. In addition, large noise is generated, and deterioration is faster. Therefore, the operation mode of air conditioning apparatus 100A is set to the prediction purification mode when the user desires. Accordingly, the user can select between lower power consumption, silent operation and longer life cycle of ion generator 10 and prevention of proliferation of molds or viruses.

In air conditioning apparatus 100, 100A in the first or second embodiment, when the operation mode is set to the prediction purification mode and the clean mode, that is, when the air in the room is in the first state or in the second state (in air conditioning apparatus 100A in the second embodiment, when the user provides an instruction), an amount of ions generated from ion generator 10 is larger than in other operation mode. Alternatively, when the operation mode is set to the prediction purification mode and the clean mode, ion generator 10 is driven so as to generate ions, whereas in other operation mode (normal state), ion generator 10 is not driven so as not to generate ions. In such a case, ions are generated only when the air in the room is in the first or second state (in air conditioning apparatus 100A in the second embodiment, when the user provides an instruction). Therefore, airborne fungi can efficiently be killed. In addition, ion generator 10 needs to be driven only when the air in the room is in the state in which airborne fungi are likely to proliferate. Accordingly, drive control of ion generator 10 is facilitated, power consumption is lowered, silent operation is set, and the life cycle of ion generator 10 can be extended.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. An ion generator, comprising:
   ion generation means for generating positive ions and negative ions;
   temperature and humidity detection means for detecting a temperature and a humidity in a room; and
   control means for
      determining whether the room is in a first state in which the detected temperature and the detected humidity are equal to or higher than a first temperature and a first humidity respectively, or a second state in which the detected temperature and the detected humidity are equal to or lower than a second temperature and a second humidity respectively, or in a third state, the temperature of the third state being between the first temperature and the second temperature, the humidity of the third state being between the first humidity and the second humidity, the first state and the second state being determined based solely on the detected temperature and the detected humidity in the room, and controlling the ion generating means to generate a larger amount of positive ions and negative ions when the room has been determined to be in the first state or in the second state as compared to when the room has been determined to be in the third state, and to selectively generate one of only negative ions or smaller amount of positive ions and negative ions when the room has been determined to be in the third state, said second temperature being lower than said first temperature, and said second humidity being lower than said first humidity.

2. The ion generator according to claim 1, further comprising:

state notification means for notification of said temperature detection result and/or said humidity detection result; and instruction accepting means for accepting an instruction to start control of said ion generation means; wherein control of said ion generation means is started in response to acceptance of the instruction by said instruction accepting means.

3. The ion generator according to claim 1, wherein said first state refers to a state in which the temperature detected by said temperature and humidity detection means is at least 25° C. and the humidity detected by said temperature and humidity detection means is at least 70%, and said second state refers to a state in which the temperature detected by said temperature and humidity detection means is at most 18° C. and the humidity detected by said temperature and humidity detection means is at most 40%.

4. The ion generator according to claim 1, further comprising:

impureness detection means for detecting impureness in the room, wherein said control means causes said ion generation means to generate negative ions more than positive ions, when the control means determines that a state of the room detected by said temperature and humidity detection means does not attain said first state and said second state, and when a prescribed degree of impureness is not detected by said impureness detection means.

5. The ion generator according to claim 4, wherein said impureness detection means includes a dust sensor.

6. The ion generator according to claim 4, wherein said impureness detection means includes an odor sensor.

7. An air conditioning apparatus, comprising:

cleaning means for lowering a degree of impureness in a room; and the ion generator according to claim 1.

8. An air conditioning apparatus, comprising:

dehumidifying and humidifying means for adjusting a humidity in a room; and the ion generator according to claim 1.

9. An air conditioning apparatus, comprising:

cooling and heating means for adjusting a temperature in a room; and the ion generator according to claim 1.

10. The ion generator according to claim 1, wherein said first state is a state in which molds are likely to proliferate, and said second state is a state in which viruses are likely to proliferate.

* * * * *